United States Patent
Amitzur et al.

(10) Patent No.: US 7,374,541 B2
(45) Date of Patent: May 20, 2008

(54) SYSTEM FOR DETERMINING ENDOTHELIAL DEPENDENT VASOACTIVITY

(75) Inventors: Giora Amitzur, Mevasseret-Zion (IL); Shmuel Einav, Herzlia (IL); Eran Peleg, Mazkeret Batia (IL); Elya Zimerman, Tel Aviv (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 0 days.

(21) Appl. No.: 10/537,913

(22) PCT Filed: Dec. 3, 2003

(86) PCT No.: PCT/IL03/01025
§ 371 (c)(1),
(2), (4) Date: Dec. 6, 2005

(87) PCT Pub. No.: WO2004/052196
PCT Pub. Date: Jun. 24, 2004

(65) Prior Publication Data
US 2006/0149152 A1 Jul. 6, 2006

Related U.S. Application Data

(60) Provisional application No. 60/431,739, filed on Dec. 9, 2002.

(51) Int. Cl.
*A61B 5/02* (2006.01)
(52) U.S. Cl. ...................................... 600/485; 600/481
(58) Field of Classification Search ................ 600/300, 600/301, 481, 485, 490, 500
See application file for complete search history.

(56) References Cited

U.S. PATENT DOCUMENTS

| | | | | | |
|---|---|---|---|---|---|
| 3,623,476 | A | * | 11/1971 | Robillard | 600/493 |
| 5,111,826 | A | * | 5/1992 | Nasiff | 600/485 |
| 5,755,229 | A | | 5/1998 | Amano et al. | |
| 6,461,305 | B1 | * | 10/2002 | Schnall | 600/485 |
| 6,939,304 | B2 | * | 9/2005 | Schnall et al. | 600/481 |
| 6,994,675 | B2 | * | 2/2006 | Sharrock | 600/500 |
| 2002/0151805 | A1 | * | 10/2002 | Sugo et al. | 600/504 |
| 2003/0036685 | A1 | * | 2/2003 | Goodman | 600/300 |

(Continued)

FOREIGN PATENT DOCUMENTS

EP  1053714  11/2000

(Continued)

OTHER PUBLICATIONS

Wilkinson et al. "Increased Augmentation Index and Systolic Stress in Type 1 Diabetes Mellitus", Q J Med., 93(7): 441-448, 2000. p. 441-442.

(Continued)

*Primary Examiner*—Robert L. Nasser, Jr.
*Assistant Examiner*—Karen E Toth

(57) ABSTRACT

A method of determining endothelial dependent vasoactivity of a subject, the method is effected by recording pressure-related signals of a plurality of locations adjacent to at least one blood vessel; extracting at least one parameter from the pressure-related signals; and using the at least one parameter to determine a change of at least one characteristic of the at least one blood vessel, the change being representative of endothelial functioning; thereby determining the endothelial dependent vasoactivity of the subject.

59 Claims, 24 Drawing Sheets

U.S. PATENT DOCUMENTS

2006/0195035 A1* 8/2006 Sun .......................... 600/503
2007/0123787 A1* 5/2007 Kitajima et al. ............ 600/509

FOREIGN PATENT DOCUMENTS

| EP | 1245183 | 2/2002 |
| --- | --- | --- |
| EP | 1360929 | 11/2003 |
| WO | WO 00/47110 | 8/2000 |
| WO | WO 02/34105 | 2/2002 |

OTHER PUBLICATIONS

Hartley et al. "Hemodynamics of Atherosclerotic Mice", Proceedings of the 22nd Annual EMBS International Conference, Chicago, Ill., IEEE, 3: 2219-2222, 2000. p. 2219.

Itoh et al. "The Therapeutic Effect of Lipo PGE1 on Diabetic Neuropathy-Changes in Endothelin and Various Angiopathic Factors", Prostaglandins, 66(3): 221-234, 2001. Abstract, § '02.5!.

Anderson et al. "Flow-Mediated and Reflex Changes in Large Peripheral Artery Tone in Humans", Circulation, 79: 93-100, 1989.

Armentano et al. "Arterial Wall Mechanics in Conscious Dogs. Assessment of Viscous, Inertial, and Elastic Moduli to Characterize Aortic Wall Behavior", Circulation Research, 76: 468-478, 1995.

Brendle et al. "Effects of Exercise Rehabilitation on Endothelial Reactivity in Older Patients With Peripheral Arterial Disease", The American Journal of Cardiology, 87: 324-329, 2001.

Anderson et al. "Close Relation of Endothelial Function in the Human Coronary and Peripheral Circulations", JACC (Journal of the American College of Cardiology), 26(5): 1235-1241, 1995.

Corretti et al. "Guidelines for the Ultrasound Assessment of Endothelial-Dependent Flow-Mediated Vasodilation of the Brachial Artery", Journal of the American College of Cardiology, 39(2): 257-265, 2002.

Corretti et al. "Correlation of Cold Pressor and Flow-Mediated Brachial Artery Diameter Responses With the Presence of Coronary Artery Disease", American Journal of Cardiology, 75: 783-787, 1995.

Cosentino et al. "Endothelial Dysfunction in Diabetes Mellitus", Journal of Cardiovascular Pharmacology, 32(Suppl.3): S54-S61, 1998.

Cosentino et al. "High Glucose Causes Upregulation of Cyclooxygenases-2 and Alters Prostanoid Profile in Human Endothelial Cells. Role of Protein Kinase C and Reactive Oxygen Species", Circulation, 107: 1017-1023, 2003.

Celermajer et al. "Cigarette Smoking Is Associated With Dose-Related and Potentially Reversible Impairment of Endothelium-Dependent Dilation in Healthy Young Adults", Circulation, 88(Part 1): 2149-2155, 1993.

Celermajer et al. "Endothelium-Dependent Dilation in the Systemic Arteries of Asymptomatic Subjects Relates to Coronary Risk Factors and Their Interactions", JACC (Journal of the American College of Cardiology), 24: 1468-1474, 1994.

Deanfield et al. "Silent Myocardial Ischaemia Due to Mental Stress", The Lancet, 2: 1001-1005, 1984.

Gage et al. "Vasoconstriction of Stenotic Coronary Arteries During Dynamic Exercise in Patients With Classic Angina Pectoris: Reversibility by Nitroglycerin", Circulation, 73: 865-876, 1986.

Gordon et al. "Atherosclerosis Influences the Vasomotor Response of Epicardial Coronary Arteries to Exercise", Journal of Clinical Investigation, 83: 1946-1952, 1989.

Hayano et al. "Decreased Magnitude of Heart Rate Spectral Components in Coronary Artery Disease. Its Relation to Angiographic Severity", Circulation, 81: 1217-1224, 1990.

Wilkinson et al. "Nitric Oxide Regulates Local Arterial Distensibility In Vivo", Circulation, 105: 213-217, 2002.

Egashira et al. "Reduction in Serum Cholesterol With Pravastatin Improves Endothelium-Dependent Coronary Vasomotion in Patients With Hypercholesterolemia", Circulation, 89: 2519-2524, 1994.

Khoury et al. "Relation of Coronary Artery Disease to Atherosclerotic Disease in the Aorta, Carotid, and Femoral Arteries Evaluated by Ultrasound", American Journal of Cardiology, 80: 1429-1433, 1997.

Malik et al. "Heart Rate Variability. Standards of Measurement, Physiological Interpretation, and Clinical Use", European Heart Journal, 17: 354-381, 1996.

Nabel et al. "Dilation of Normal and Constriction of Atherosclerosis Coronary Arteries Caused by the Cold Pressor Test", Circulation, 77(1): 43-52, 1988.

Nafz et al. "Endogenous Nitric Oxide Buffers Blood Pressure Variability Between 0.2 and 0.6 Hz in the Conscious Rat", American Journal of Physiology (Heart Circulation Physiology), 272: H632-H637, 1997.

Parati et al. "Spectral Analysis of Blood Pressure and Heart Rate Variability in Evaluating Cardiovascular Regulation. A Critical Appraisal", Hypertension, 25: 1276-1286, 1995.

Pelat et al. "Rosuvastatin Decreases Caveolin-1 and Improves Nitric Oxide-Dependent Heart Rate and Blood Pressure Variability in Apolipoprotein E-/- Mice In Vivo", Circulation, 107: 2480-2486, 2003.

Persson "Spectrum Analysis of Cardiovascular Time Series", American Journal of Physiology—Regulatory, Integrative and Comparative Physiology, 273: 1201-1210, 1997.

Perticone et al. "Prognostic Significance of Endothelial Dysfunction in Hypertensive Patients", Circulation, 104: 191-196, 2001.

Joannides et al. "Nitric Oxide Is Responsible for Flow-Dependent Dilation of Human Peripheral Conduit Arteries In Vivo", Circulation, 91: 1314-1319, 1995.

Sorensen et al. "Atherosclerosis in the Human Brachial Artery", JACC (Journal of the American College of Cardiology), 29(2): 318-322, 1997.

Stadler et al. "Measurement of the Time Course of Peripheral Vasoactivity: Results in Cigarette Smokers", Atherosclerosis, 138: 197-205, 1998.

Vanhoutte "Endothelial Dysfunction and Atherosclerosis", European Heart Journal, 18(Suppl.E): E19-E29, 1997.

Vita et al. "Patients With Evidence of Coronary Endothelial Dysfunction as Assessed by Acetylcholine Infusion Demonstrate Marked Increased in Sensitivity to Constrictor Effects of Catecholamines", Circulation, 85: 1390-1397, 1992.

Vogel et al. "Changes in Flow-Mediated Brachial Artery Vasoactivity With Lowering of Desirable Cholesterol Levels in Healthy Middle-Aged Men", American Journal of Cardiology, 77: 37-40, 1996.

Vogel "Coronary Rsik Factors, Endothelial Function, and Atherosclerosis: A Review", Clinical Cardiology, 20: 426-432, 1997.

Widlansky et al. "The Clinical Implications of Endothelial Dysfunction", Journal of the American College of Cardiology, 42(7): 1149-1160, 2003.

Zeiher et al. "Coronary Vasomotion in Response to Sympathetic Stimulation in Humans: Importance of the Functional Integrity of the Endothelium", JACC (Journal of the American College of Cardiology), 14(5): 1181-1190, 1989.

* cited by examiner time in minutes

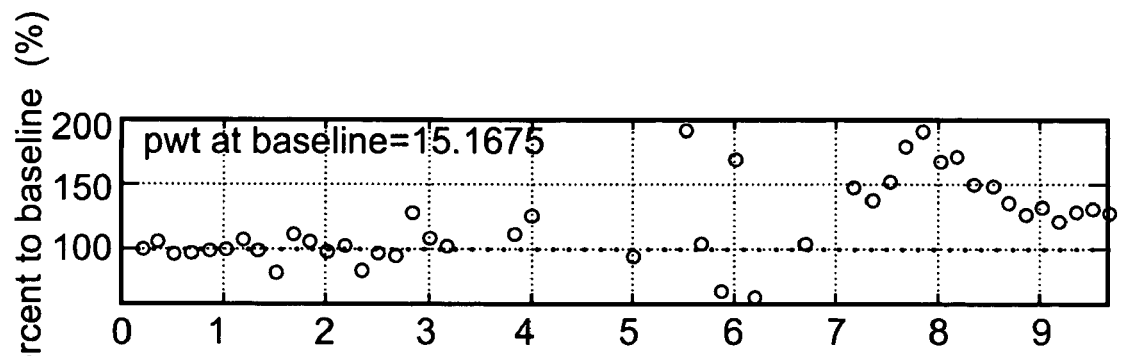
Fig. 13a
Fig. 13b
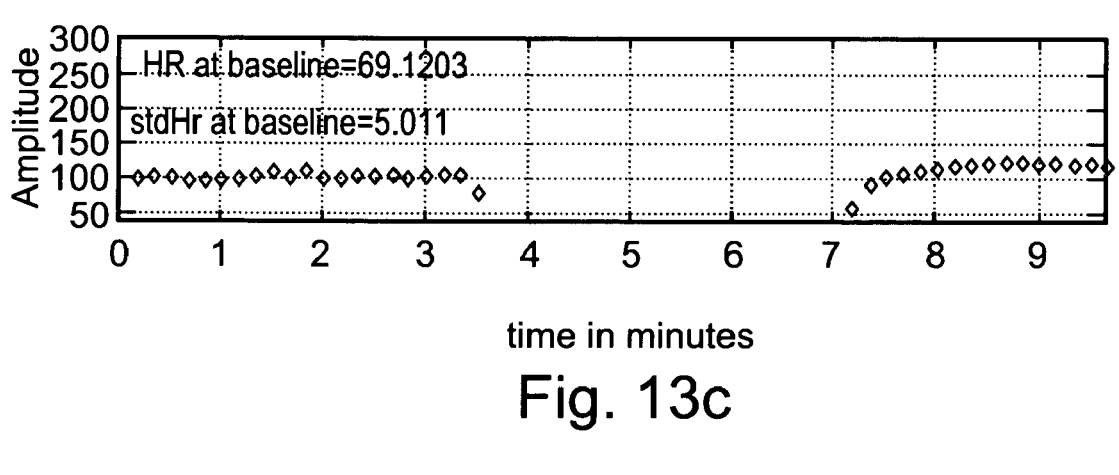
time in minutes
Fig. 13c time in minutes time in minutes time in minutes

SYSTEM FOR DETERMINING ENDOTHELIAL DEPENDENT VASOACTIVITY

RELATED PATENT APPLICATION

This application is a National Phase Application of PCT/IL03/01025 having International Filing Date of 3 Dec. 2003, which claims the benefit of U.S. Provisional Patent Application No. 60/431,739 filed 9 Dec. 2002.

FIELD AND BACKGROUND OF THE INVENTION

The present invention relates to measuring endothelial dependent vasoactivity and, more particularly, to a non-invasive method and system for determining endothelial dependent vasoactivity.

Hemodynamics is a subchapter of cardiovascular physiology, which deals with the forces the heart has to develop in order to circulate blood throughout the cardiovascular system. To a physician, these forces are manifested as blood pressure and blood flow paired values measured simultaneously at different points of the cardiovascular system.

The flow of blood through the vasculature has a pulsatile nature. When the heart contracts, part of the blood contained within the left ventricle is squeezed into the aorta from which the blood flows into the entire cardiovascular system. Since blood is an incompressible fluid, when it is squeezed into the vasculature, which exhibits a resistance to blood flow, blood pressure is generated. During ventricular contraction the arterial blood pressure increases to its highest, the systolic level. When the left ventricle is refilled with oxygenated blood from the lungs during the relaxation phase of the cardiac cycle (the diastole), and the ventricle is disconnected from the vasculature by the aortic valve, the pressure in the vasculature decreases to its lowest level.

The amount of blood which is pumped with each heartbeat, also known as the stroke volume, normalized by body surface area is known as the Stroke Index (SI). The mean value of blood pressure is called the Mean Arterial Pressure (MAP). The values of SI and MAP are a result of modulation by several hemodynamic modulators: (i) intravascular volume, (ii) inotropy, (iii) Starling effect and (iv) vasoactivity.

Intravascular volume is the amount of fluid circulating in the vasculature. This modulator can be affected, for example, by dehydration, diuresis, venoconstriction of the spleen, volume overload due to heart or kidney failure and the like.

Inotropy is the ability of the cardiac muscle to contract. Myocytes are the only muscle cells which are able to vary the strength of contraction. Inotropy can be affected by exercise, stress and pharmaceutical agents, which increase the strength of myocardial contractions, or by cardiac diseases such as heart failure, which is expressed by decrease of the strength of contractions. The myocardial contractility is controlled by positive and negative inotropes which instantaneously affect the level of inotropic state. Changes in inotropy alter the rate of force and pressure development by the ventricle.

The heart has the intrinsic capability of increasing its force of contraction when preload is increased. The preload is related to the sarcomere length via the well known Starling law.

Vasoactivity referrers to the ability of blood vessels to expand and contract. Through vasoactivity the body controls the flow of blood through individual organs, accommodate the variation in blood flow and regulate arterial pressure.

The endothelium-dependent relaxation of blood vessels is due to the release of potent non-proslanoid vasodilator substances by the endothelium (the inner most cellular layer of the blood vessel) surrounding the blood vessel. The endothelium-derived relaxing factor is believed to be nitric oxide (NO), which is released by different stimuli substances produced during platelet aggregation. The endothelial action of thrombin and platelet products is crucial for the protective role played by the normal endothelium against unwanted coagulation. Therefore, local platelet aggregation, with the associated release of serotonin and ADP, together with the production of thrombin, leads to a major local release of NO. The NO diffuses towards the underlying vascular smooth muscle, induces its relaxation and thus contributes to the dilatation of the artery. The release of NO to the blood vessel also inhibits platelet adhesion at the endothelium blood interface, exerts a major feedback on platelet aggregation, thereby eliminates the imminent danger of vascular occlusion. In addition, the endothelial barrier prevents the platelet derived vasoconstrictor substances from reaching the smooth muscle. NO can also be released by other stimuli like flow mediated vasoactivity and increased sympathetic activity (alpha receptor stimulation).

It is recognized that dysfunction of endothelial dependent vasoactivity, also known as endothelial dysfunction, is an early event in the pathogenesis of cardiovascular disease. Endothelial dysfunction and coronary artery disease are also linked to over-weight, obesity, hypertension, hypercholesterolemia, hyperlipidemia, diabetes mellitus, cigarette smoking and homocysteine. In addition, the vascular endothelium plays a fundamental role in several processes related to thrombosis. Impaired endothelium function may also promote the development of atherosclerosis through its effects on vaso-regulation, platelet and monocyte adhesion.

Several studies have demonstrated that elevated concentration of total cholesterol and low density lipoprotein cholesterol are associated with impaired endothelial function, independent of the presence of coronary heart disease [Robert A. Vogel, "Coronary risk factors, Endothelial function, and atherosclerosis: A review," Clin. Cardiol 1997, 20:426-432; Robert A. Vogel et al., "Changes in flow-mediated brachial artery vasoactivity with lowering of desirable cholesterol levels in healthy middle aged men," The American journal of cardiology 1996, 77; Kensuke Egashira et al., "Reduction in serum cholesterol with pravastatin improves endothelium dependent coronary vasomotion in patients with hypercholesterolemia," Circulation 1994, 89 No 6]. In addition, decreased concentrations of high-density lipoprotein cholesterol and an elevated ratio of total to high-density lipoprotein cholesterol have also been associated with endothelial dysfunction.

Cigarette smoking profoundly impairs endothelial function [Robert W. stadler et al., "Measurment of the time course of peripheral vasoactivity: results in cigarette smokers," Atherosclerosis 1998 138:197-205; David S. Celermajer et al., "Cigarette smoking is associated with dose-related and potentially reversible impairment of endothelium-dependent dilation in healthy young adults," Circulation 1993, 88, No 5 part 1]. Endothelial function is reduced in both active and passive smokers in a dose dependent manner. Smoking cessation is associated with improvement in endothelial function.

Endothelial dysfunction increases in men over the age of about 40 and in women after the age of about 55, whether or not other coronary risk factors are present. The specific cause of the decrease in endothelial function with age is yet unknown. Estrogen appears to be a major factor associated with gender differences in age-related endothelial function.

Other factors which affect endothelial function include hypertension [Perticone F, et al., "Prognostic significance of endothelial dysfunction in hypertensive patients," Circulation 2001, 104:191-196], diabetes [Cosentino F et al., "Endothelial dysfunction in diabetes mellitus," J Cardiovasc Pharmacol, 1998, 32:54-61; Cosentino F et al., "High glucose causes upregulation of Cyclooxygenase-2 and alters prostanoid profile in human endothelial cells. Role of protein kinase C and reactive oxygen species," Circulation 2003, 107:1017-1023], diet and physical exercise [Brendle D et al., "Effects of exercise rehabilitation on endothelial reactivity in older patients with peripheral arterial disease," Am J Cardiol 2001, 87:324-329].

The full range of different diseases associated with endothelial dysfunction, the nature of endothelial abnormalities and the effects of potential treatments on vasoactivity are yet to be determined. Nevertheless, the measurement of arterial endothelium function is of utmost importance for the purpose of diagnosing endothelial dysfunction related diseases at early stage, for example for diagnostic assessment of atherosclerothic disease in the pre-stenotic stages [Vanhoutte. P. M., "Endothelial dysfunction and atherosclerosis," Eur Heart J, 1997:18 (sup E) E19-E29; Robert A. Vogel, 1997 ibid; Mary C. Corretti et al., "Guidelines for the ultrasound assessment of endothelial-dependent flow-mediated vasodilatation of the brachial Artery," JACC 2002, 39:257-65; Widlansky M E, Gokee N, Keaney J F Jr, Vita J A, J, "The clinical implications of endothelial dysfunction," J Am Coll Cardiol 2003, 42:1149-60].

Normal release of NO prevents and/or attenuates arteriosclerosis as well as other major factors such as thrombosis [Robinson Joannides et al., "Nitric oxide is responsible for flow-dependent dilatation of human peripheral conduit arteries in vivo," Circ. 1995, 91:1311-12; Ian B. Wilkson et al., "Nitric oxide regulates local arterial distensibility in-vivo," Circ. 2002, 105:213-217].

Many studies have demonstrated that endothelial dysfunction in coronary arteries is concomitant with impaired endothelial brachial, radial and the carotid dysfunction [Corretti et al., 2002 ibid; Tod J. Anderson et al., "Close relation of endothelial function in the human coronary and peripheral circulations," JACC 1995, 26:1235-41; David S. Celermajer et al., "Endothelium-dependent dilation in the systemic arteries of asymptomatic subjects relates to coronary risk factors and their interaction," JACC 1994, 24:1468-74; Sorensen K E et al., "Atherosclerosis in the human brachial artery," JACC 1997, 29:318-22]. In addition, it was found that coronary artery disease is related to atherosclerothic disease in the aorta and the carotid artery [Khoury Z et al., "Relation of coronary artery disease to atherosclerothic disease in the aorta, carotid, and femoral arteries evaluated by ultrasound," Am J Cardiol 1997, 80:1429-1433].

Assessment of endothelium dependent vasoreactivity (EDV) in coronary arteries may be performed by measurements of changes in peripheral arterial diameter due to pharmacological or mechanical stimuli.

One method for measuring the inner diameter of a blood vessel is by an intravascular ultrasound device having an intravascular catheter and an ultrasound transducer array mounted thereon. The intravascular catheter is inserted directly into the artery of interest to thereby determine its inner diameter.

Such a device is highly invasive, expensive and requires costly additional technical expertise to operate.

Another known device for measuring the intravascular diameter of a blood vessel has an elongated flexible sheath and a catheter which is longer than the sheath. The sheath has an outer diameter which is less than the intravascular diameter. The catheter proximal end extends outwardly from the proximal end of the sheath and includes a measuring scale directly proportional to a position of a sensor extending from the catheter. When the sheath is inserted into the blood vessel and the catheter is moved inwardly relative to the sheath, the intravascular diameter can be read directly from the measuring scale.

This device, however, although simple and not expensive, is still highly invasive and lacks the necessary accuracy for the purpose of determining vasoactivity.

Also known in the art are non-invasive methods for the measurement of arterial diameter by high resolution non-invasive ultra-sound systems. In one such method the physician operates an ultrasound transducer to obtain appropriate ultrasound images of the brachial artery for measuring artery diameter thereof. This method, however, is time consuming, and requires a highly trained physician or technician to hold the transducer stably during the measurement.

In another such method, an automatic measurement system having a robot arm manipulating ultrasound imaging probe is used. The system automatically navigates the ultrasound imaging probe to an appropriate position and measure changes in diameter of brachial artery with improved reproducibility compared with manual measurement.

This procedure, however, is very costly, requiring highly practiced personnel and equipment, and thereby lacks the ability to become a standard clinical procedure in the assessment of endothelial dysfunction in large high-risk populations.

The autonomic nervous system (ANS) plays a cardinal role in the control of cardiovascular function. Heart rate, heart excitability and contractility are under the constant influence of the parasympathetic-sympathetic balance. Parasympathetic nerves and sympathetic fibers innervate the sino-atrial node; the parasympathetic influence is inhibitory while the sympathetic influence is excitatory. The parasympathetic fibers to the SA node are driven by inhibitory and excitatory inputs from peripheral receptors (baroreceptors, chemoreceptors, cardiac, pulmonary and airway receptors). Behavioral adaptive influence of the heart rate at the sinus node is mediated by supramedullary inputs to the cardiovagal neurons. The origin of the sympathetic innervation of the heart is located at the T2-T5 segment of the spinal cord and the preganglionic fibers synapse in the cervical ganglia.

Normal cardiac function is regulated by the complex balance of the sympathetic and parasympathetic outflows to the heart. This balance is also responsible for the susceptibility to arrhythmias: while vagal activity has a protective role, sympathetic activity lowers the threshold to ventricular fibrillation. Normal heart function, heart rate included, is modulated by the fluctuations in the sympathetic and parasympathetic flow to the heart. These fluctuations induce beat-to-beat variability in heart rate and arterial pressure. Hence, the analysis of the instantaneous fluctuations in cardiovascular variables supplies valuable information on the autonomic control in an intact organism.

Over the past two decades, analysis of electrocardiogram (ECG) signals in general and Heart-Rate-Variability (HRV) in particular, have been used to quantify the behavior of the ANS [Malik et al., "Guidelines. Heart rate Variability," Eur Heart J 1996, 17:354-381]. It was found that about 5 minutes recording of HRV are sufficient for detecting possible existence of coronary artery disease [Parati et al., "Spectral analysis of blood pressure and heart rate variability in evaluating cardiovascular regulation. A critical appraisal," Hypertension 1995, 25(6): 1276-86; Hayano J et al., "Decreased magnitude of heart rate spectral components in coronary artery disease and its relation to angiographic severity," Circulation 1990, 81(4):1217-24].

There is thus a widely recognized need for, and it would be highly advantageous to have, a simple, cost effective, non-invasive method and system for determining endothelial abnormal function.

SUMMARY OF THE INVENTION

According to one aspect of the present invention there is provided a method of determining endothelial dependent vasoactivity of a subject, the method comprising: recording pressure-related signals of a plurality of locations adjacent to at least one blood vessel; extracting at least one parameter from the pressure-related signals; and using the at least one parameter to determine a change of at least one characteristic of the at least one blood vessel, the change being representative of endothelial functioning; thereby determining the endothelial dependent vasoactivity of the subject.

According to further features in preferred embodiments of the invention described below, the method further comprising determining an autonomic nervous system activity of the subject.

According to still further features in the described preferred embodiments the determining of the autonomic nervous system activity is by heart rate variability analysis of the pressure-related signals.

According to still further features in the described preferred embodiments the determining of the autonomic nervous system activity comprises recording electrocardiogram signals of a chest of the subject and performing heart rate variability analysis of the electrocardiogram signals, thereby determining the autonomic nervous system activity.

According to still further features in the described preferred embodiments the method further comprises determining a pre-ejection period and valve-artery period.

According to still further features in the described preferred embodiments the valve of the valve-artery period is an aortic valve and the artery of the valve-artery period is a carotid artery.

According to still further features in the described preferred embodiments the determination of the pre-ejection period and the valve-artery period, comprises determining an elapsed time between peaks of the electrocardiogram signals and peaks of the pressure-related signals.

According to still further features in the described preferred embodiments the peaks of the electrocardiogram signals comprise QRS peaks.

According to still further features in the described preferred embodiments the method further comprising stimulating the at least one blood vessel.

According to still further features in the described preferred embodiments the stimulating of the at least one blood vessel is effected by a procedure selected from the group consisting of a mechanical stimulation, a thermal stimulation a chemical stimulation, an electrical stimulation a mental stress stimulation and a physical exercise stimulation.

According to still further features in the described preferred embodiments the stimulating of the at least one blood vessel is by applying external pressure on the at least one blood vessel.

According to still further features in the described preferred embodiments the stimulating of the at least one blood vessel is by reducing a temperature of the at least one blood vessel.

According to still further features in the described preferred embodiments the method further comprising correlating the endothelial functioning and the autonomic nervous system activity, so as to obtain a correlation function, and using the correlation function to at least preliminarily determine the endothelial dependent vasoactivity of the subject.

According to still further features in the described preferred embodiments the recording of the pressure-related signals is by piezoelectric ceramic elements.

According to still further features in the described preferred embodiments the recording of the pressure-related signals is by a membrane-based sensor.

According to still further features in the described preferred embodiments an electrate microphonethe membrane-based sensor is an electrate microphone.

According to still further features in the described preferred embodiments the extracting of the at least one parameter comprises: (a) scanning pressure-related signals recorded of a first location and detecting a first peak; (b) scanning pressure-related signals recorded of a second location and detecting a second peak corresponding to the first peak; (c) measuring an elapsed time between the first peak and the second peak; and (d) repeating the steps (a)-(c) at least once.

According to another aspect of the present invention there is provided a system for determining endothelial dependent vasoactivity of a subject, the system comprising: an arrangement of sensors for recording pressure-related signals of a plurality of locations adjacent to at least one blood vessel; a processing unit operable to receive, record and process the pressure-related signals; the processing unit being designed and programmed to extract at least one parameter from the pressure-related signals, and to use the at least one parameter to determine a change of at least one characteristic of the at least one blood vessel, the change being representative of endothelial functioning.

According to further features in preferred embodiments of the invention described below, the system further comprising electronic-calculation functionality for determining an autonomic nervous system activity of the subject.

According to still further features in the described preferred embodiments the processing unit is operable to calculate heart rate variability from the pressure-related signals thereby to determine the autonomic nervous system activity.

According to still further features in the described preferred embodiments the system further comprising at least one electrocardiogram lead designed connectable to a chest of the subject.

According to still further features in the described preferred embodiments the processing unit is operable to calculate heart rate variability from electrocardiogram signals sensed by the at least one electrocardiogram lead, thereby to determine the autonomic nervous system activity.

According to still further features in the described preferred embodiments the system further comprising a spectral analyzer for analyzing the at least one parameter and obtaining a frequency decomposition of the at least one parameter, the frequency decomposition being representative of the endothelial dependent vasoactivity of the subject.

According to still further features in the described preferred embodiments the system further comprising a mechanism for stimulating the at least one blood vessel.

According to still further features in the described preferred embodiments the mechanism for stimulating the at least one blood vessel is selected from the group consisting of a mechanical mechanism, a thermal mechanism, an electrical mechanism and a mechanism for generating mental stress.

According to still further features in the described preferred embodiments the mechanism is operable to apply external pressure on the at least one blood vessel.

According to still further features in the described preferred embodiments the mechanism comprises a sphingomanometer.

According to still further features in the described preferred embodiments the mechanism is operable to reduce a temperature of the at least one blood vessel.

According to still further features in the described preferred embodiments the mechanism is a bath or a cuff of fluid, the fluid being at a predetermined temperature.

According to still further features in the described preferred embodiments the sensors are piezoelectric ceramic elements.

According to still further features in the described preferred embodiments the sensors membrane-based are sensors.

According to still further features in the described preferred embodiments the sensors are electrate microphones.

According to still further features in the described preferred embodiments the method further comprising obtaining a frequency decomposition of the at least one parameter, and using the frequency decomposition for determining the endothelial dependent vasoactivity of the subject.

According to still further features in the described preferred embodiments the at least one parameter is selected from the group consisting of an amplitude of the pressure-related signals, a width of the pressure-related signals and an elapsed time between two peaks of the pressure-related signals.

According to still further features in the described preferred embodiments the method further comprising obtaining a frequency decomposition of the amplitude, and using the frequency decomposition for determining the endothelial dependent vasoactivity of the subject.

According to still further features in the described preferred embodiments the method further comprising obtaining a frequency decomposition of the width, and using the frequency decomposition for determining the endothelial dependent vasoactivity of the subject.

According to still further features in the described preferred embodiments the method further comprising obtaining a frequency decomposition of the elapsed time, and using the frequency decomposition for determining the endothelial dependent vasoactivity of the subject.

According to still further features in the described preferred embodiments the at least one characteristic of the at least one blood vessel is selected from the group consisting of a radius of the at least one blood vessel and an elastic modulus of the at least one blood vessel.

According to yet another aspect of the present invention there is provided a method of determining endothelial dependent vasoactivity of a subject, the method comprising: (a) applying a first stimulus to at least one blood vessel; (b) measuring a pulse wave velocity in the at least one blood vessel; (c) determining an autonomic nervous system activity of the subject; (d) correlating the pulse wave velocity and the autonomic nervous system activity, so as to obtain a correlation function having an index; and (e) if the index has a predetermined value then: (i) applying a second stimulus on the at least one blood vessel; and (ii) repeating steps (b)-(c); thereby determining the endothelial dependent vasoactivity of the subject.

According to further features in preferred embodiments of the invention described below, step (e) further comprises applying the second stimulus on at least one additional blood vessel and repeating the steps (b)-(c) for the at least one additional blood vessel.

According to still further features in the described preferred embodiments the first and the second stimuli are each independently selected from the group consisting group consisting of a mechanical stimulus, a thermal stimulus, a chemical stimulus, an electrical stimulus, a mental stress stimulus and a physical exercise stimulus.

According to still further features in the described preferred embodiments the stimulus comprises external pressure.

According to still further features in the described preferred embodiments the stimulus comprises temperature reduction.

According to still further features in the described preferred embodiments the measuring a pulse wave velocity is by recording pressure-related signals using piezoelectric ceramic elements.

According to still further features in the described preferred embodiments the wherein the measuring a pulse wave velocity is by recording pressure-related signals using a membrane-based sensor.

According to still further features in the described preferred embodiments the at least one blood vessel is selected from the group consisting of a brachial artery, a radial artery and a carotid artery.

The present invention successfully addresses the shortcomings of the presently known configurations by providing a method and system for assessing endothelial dependent vasoactivity enjoying properties far exceeding prior art technologies.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 13a-c show the elapsed time (FIG. 13a), standard deviation (FIG. 13b) and amplitude (FIG. 13c) during sitting position of a subject who has been diagnosed by US measurements as having normal endothelial function.

DESCRIPTION OF THE PREFERRED EMBODIMENTS

Figure 1:
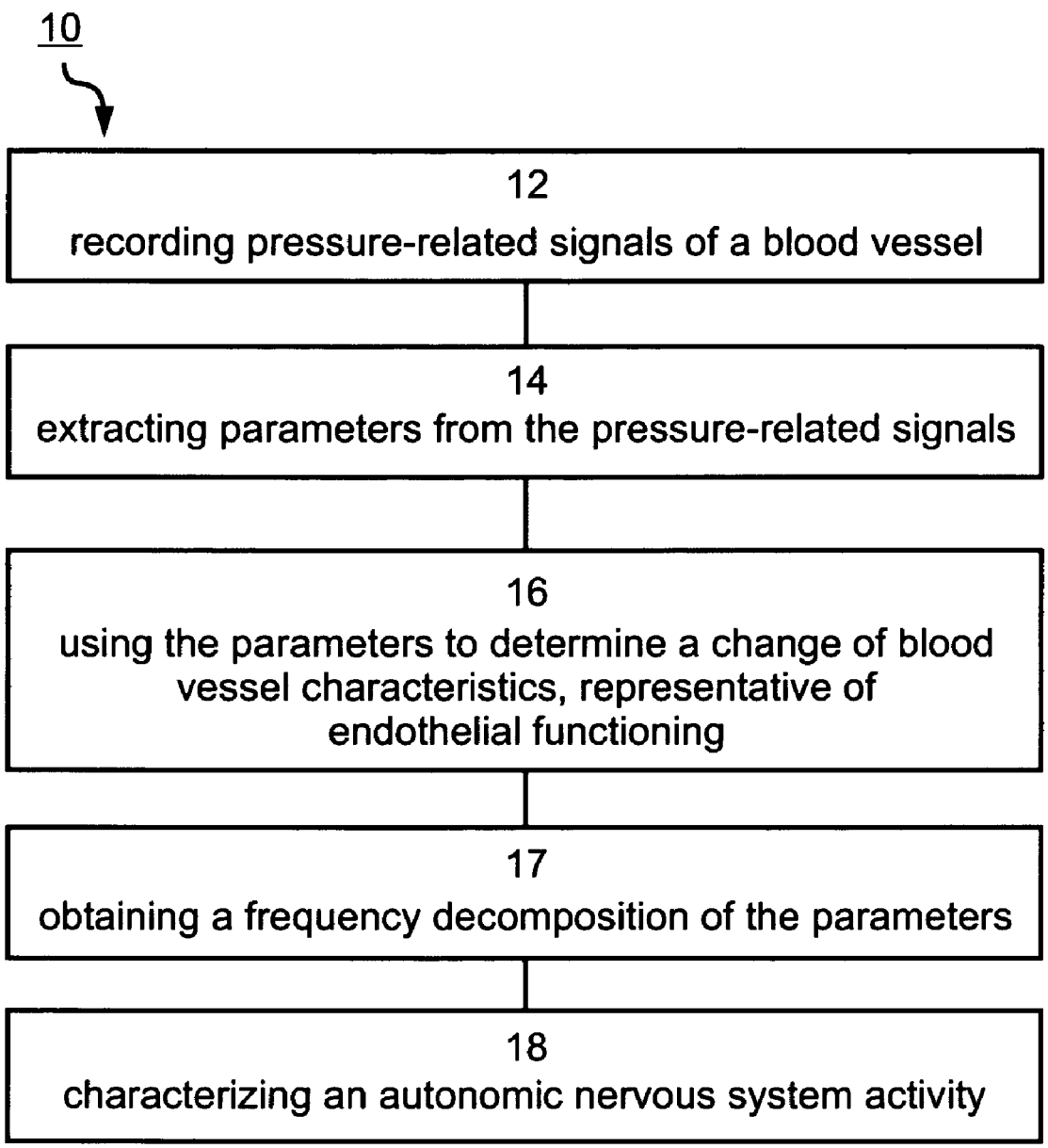
FIG. 1 is a flowchart diagram of a non-invasive method of determining endothelial dependent vasoactivity, according to a preferred embodiment of the present invention.

The present invention is of a non-invasive method and system for determining endothelial dependent vasoactivity which can be used in early stage diagnosis of endothelial dysfunction related diseases. Specifically, the present invention can be used to screen and diagnose large population and to differentiate between subjects being in different stages and combinations of endothelial and coronary artery dysfunction. For example, the present invention can be used to diagnose pathogenesis of cardiovascular disease, atherosclerosis and the like.

The principles and operation of a method and system for determining endothelial dependent vasoactivity of a subject according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

A pulsatile flow of fluid through an elastic conduit is accompanied by elevated friction and normal forces between the conduit and the fluid. Such flow is characterized by dominant peripheral energy propagation, i.e., along the wall of the elastic conduit. The speed of a pressure pulse propagating through the conduit is determined by the elastic and geometric properties of the conduit's wall as well as by the physical properties of the fluid.

In an artery, the velocity of the pressure pulse generated by ventricular ejection can be calculated using Moens-Korteweg model, according to which the square of the pulse wave velocity, c, equals the area of the artery divided by the density of the blood and the mechanical compliance of the artery. The mechanical compliance, defined as the derivative of the cross-sectional area with respect to the pressure, is, to a good approximation $2R/(E h)$, where, R is the radius of the artery, h is the thickness of the artery's wall and E is its Young modulus. The pulse wave velocity is therefore given by the following equation, commonly known as the Moens-Korteweg equation:

$$c = \sqrt{\frac{Eh}{2\rho R}}, \quad \text{(EQ. 1)}$$

where $\rho$ is the density of the blood.

The present invention exploits the relation between the pulse wave velocity and the geometrical and elastic properties of the arterial wall for the purpose of determining vasoactivity.

Referring now to the drawings, FIG. 1 is a flowchart diagram of a non-invasive method 10 of determining endothelial dependent vasoactivity of a subject, according to one aspect of the present invention.

In a first step of method 10, designated by Block 12, pressure-related signals are recorded of several locations adjacent to one or more blood vessels. The pressure-related signals are typically electrical signals, which are recorded, e.g., using piezoelectric ceramic elements or membrane-based sensors, such as, but not limited to, electrate microphones. As further detailed and exemplified hereinunder and in the Examples section that follows, these pressure-related signals are related to the pulse wave velocity of the blood, hence can be used to characterize the geometrical and elastic properties of the arterial wall.

In a second step of method 10, designated by Block 14, at least one parameter is extracted from the pressure-related signals. Representative examples of extracted parameters include, without limitation, amplitude of the signals, width thereof and/or elapsed time between peaks of two pressure-related signals.

The amplitude parameter is preferably defined as the height of the signal above a predetermined zero-level.

The width parameter is preferably defined as the distance between two points of equal height or two inflection points on the same signal.

The elapsed time parameter is preferably defined as the elapsed time between two peaks of signals recorded of two different locations, either two locations near the same blood vessels or near different blood vessels. The elapsed time parameter is directly related to the pulse wave velocity. More specifically, knowing the transit time, t, of the pulse wave between two locations and its traveling distance, L, one can calculate the pulse wave velocity, by division (L/t) or differentiation (dL/dt).

Any of the above parameters may be extracted from the signals by any appropriate method known in the art, such as, but not limited to, correlation method, peak detection, mathematical fitting (e.g., polynomial fitting), frequency decomposition (e.g., Fourier transform), data folding and the like. According to a preferred embodiment of the present invention the extraction is performed a plurality of times, so as to obtain, for each type of parameter, a plurality of values which may then be averaged.

In a third step of method 10, designated by Block 16, the parameter(s) are used to determine a change of one or more blood vessel characteristics, e.g., geometrical or elastic properties thereof. Such a change characterizes endothelial function of the blood vessel.

For example, due to collagen fiber recruitment in the arterial wall which is increased during the dilatation stage of the artery, the elapsed time parameter is sensitive to arterial radius changes at the initial stage of arterial dilatation, and the amplitude parameter is sensitive to arterial radius changes at relatively large arterial dilatation. Thus, a judicious use of the elapsed time parameter and the amplitude parameter allows an accurate and reliable measurement of changes in the arterial radius at a wide range of values.

Although radius changes are the favored blood vessel characteristics in the according to the presently preferred embodiment of the invention, other blood vessel characteristics, e.g., elastic modulus are not excluded.

For small radii, the elastic modulus of the blood vessel is, to a good approximation, a constant quantity. On the other hand, for large radii the elastic module becomes radius-dependent [Armentano R. L et al., "Arterial wall mechanics in conscious dogs—assessment of viscous, internal, and elastic moduli to characterize aortic wall behavior," Circulation Research 1995, 76:468-78], and can be determined using the elapsed time parameter.

Generally, the radius, thickness and elasticity of the blood vessel are interrelated by the following equation, directly derived from Equation 1, above:

$$\frac{c_2}{c_0} = \sqrt{\frac{E_2 h_2 R_0}{E_0 h_0 R_2}}, \quad \text{(EQ. 2)}$$

where the subscripts "0" and "2" represent values at different states (i.e., relaxation and contraction) of the blood vessel. A consequence of Equation 2 is that as the artery's radius increase the pulse wave velocity decreases. In terms of elapsed time, a decrease in the pulse wave velocity is manifested as an increment of the elapsed time between two peaks of the signals.

Figure 2:
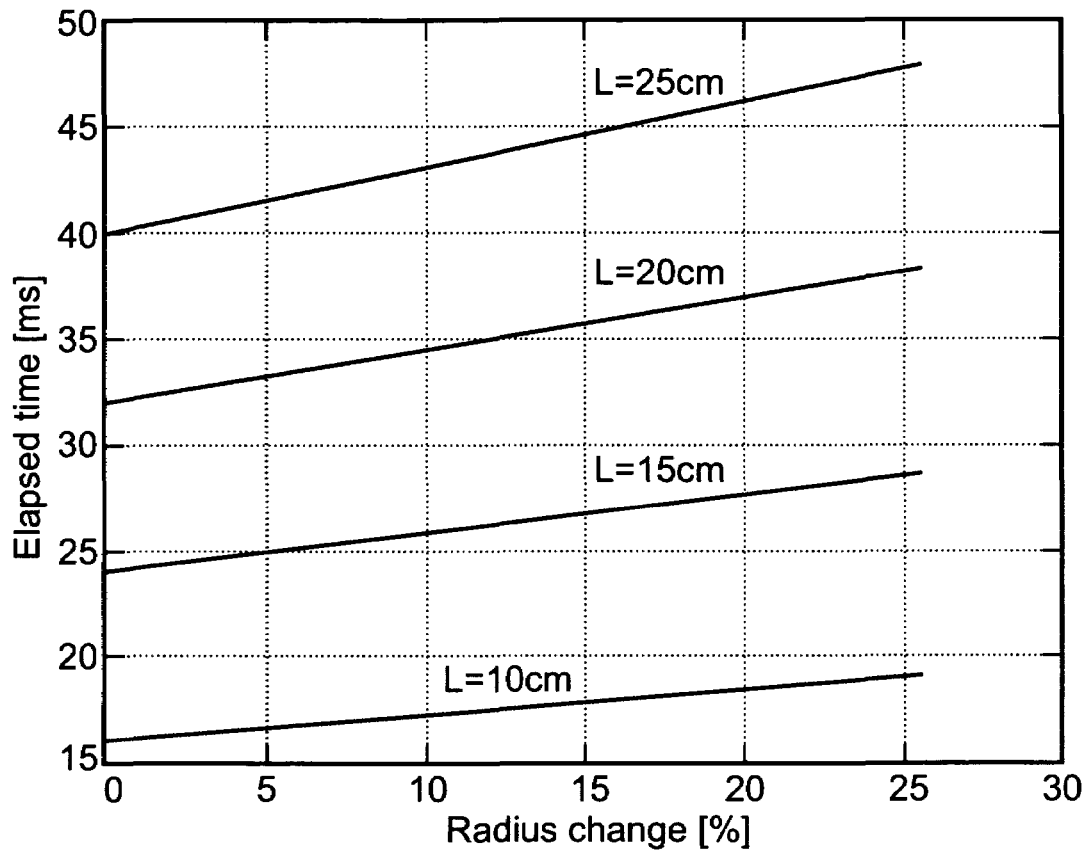
FIG. 2 shows theoretical estimations of relative changes in the elapsed time between two peaks of pressure-related signals, as a function of changes in arterial radius, assuming an approximately constant Young modulus.

FIG. 2 shows theoretical estimations of the relative changes in the elapsed time as a function of changes in arterial radius, assuming an approximately constant Young modulus. The different lines in FIG. 2 correspond to different effective blood flow distances, L. The calculations were performed using typical initial radius and elasticity modulus, taken from the literature.

It will be therefore appreciated that the measurement of the above parameters is related to the geometrical and elastic properties of the blood vessel, hence allows the determination of the endothelial dependent vasoactivity.

NO is known to have a buffering influence on arterial pressure variability. An acute change of arterial pressure alters shear stress, thus modifying NO generation and release. Subsequent vasodilatation or vasoconstriction occurs in response to the varying NO levels, which in turn readjust vascular resistance to reduce arterial pressure variability. NO acts rapidly: it diffuses out of the endothelium to the subjacent vascular smooth muscle cells, where it causes vaso-relaxation within seconds. Thus, NO can affect the regulation of blood pressure more rapidly than the arterial baroreflex. [Persson P B., "Spectral analysis of cardiovascular time series," Am J Physiol, 273:R1201-R1210, 1997]. For example, it has been found in rats that after NO inhibition, the power in the range of above 0.2 Hz increases significantly, indicating that NO buffers blood pressure variability at these frequencies [Nafz B et al., "Endogenous nitric oxide buffers blood pressure variability between 0.2 and 0.6 Hz in the conscious rat," Am J Physiol 272:H632-H637,1997].

In addition, in mice, restoration of NO function improved blood pressure and heart rate variability (Pelat M. et al., "Rosuvastatin decreases caveolin-1 and improves nitric oxide-dependent heart rate and blood pressure variability in apolipoprotein E-/- mice in vivo," Circulation 107:2480-2486,2003).

Hence, the above parameters can be further analyzed for the purpose of obtaining other observables sensitive to the above physiological mechanism. Many analysis procedures are contemplated by the present invention, including, without limitation, spectral analysis, modulation analysis and the like.

Referring again to FIG. 1, according to a preferred embodiment of the present invention, the method further comprises an optional step, designated in FIG. 1 by Block 17, in which a frequency decomposition is obtained from one or more of the parameters, e.g., by performing spectral analysis. The obtained frequency decomposition can be used for determining the endothelial dependent vasoactivity of the subject. For example, endothelial dysfunction can be determined when the frequency decomposition includes higher power in the high frequency range, e.g., above about 0.15 Hz. Alternatively, endothelial dysfunction can be diagnosed when a decrease in power in lower frequency ranges (e.g., below about 0.12 Hz, below about 0.08 Hz, or below 0.06 Hz). For subjects having endothelial dysfunction, such increment of power in the high frequency range can be followed by increased variability of the elapsed time and the amplitude parameters.

While reducing the present invention to practice it has been uncovered that the above procedure may be improved by an additional step, designated by Block 18, in which an autonomic nervous system activity of the subject is characterized. Heart rate changes, commonly referred to as heart rate variability, are known to be a direct consequence of alterations in the activity of autonomic nervous system. Hence, according to a preferred embodiment of the present invention, the autonomic nervous system characterization is done by heart rate variability analysis.

Heart rate variability may be determined in more than one way. Hence, in one embodiment, the heart rate variability is determined from the pressure-related signals. For example, the pressure-related signals can be divided into segments, preferably equally distributed, where in each segment the mean heart rate is calculated by subtraction of subsequent peak times. The heart rate variability is then defined as the standard deviation of the heart rate in each segment. Typical duration for each segment, according to a preferred embodiment of the present invention, is between 5 seconds and 15 seconds, inclusive.

In another embodiment, heart rate variability is obtained by a different measurement, which may be, for example, electrocardiogram measurement or any other procedure for recording electrical signals of the chest of the subject. A known device for determining heart rate variability is a Holter monitor, which is a recorder for a continuous, typically twenty-four hour, electrocardiographic recording of the heart rate.

Many methods are known in the art for determining heart rate variability from the electrocardiogram signal. For example, heart rate variability may be determined by extracting a series of cardiac R-R intervals from the electrocardiogram signals. Electrocardiogram signals include, inter alia, the so-called P waves, T waves and QRS complexes, which QRS complexes include Q waves, R-waves and S waves. An R-R interval is the elapsed time between two successive R-waves of the electrocardiogram signals. Two known definitions exist for the R peak: (i) the highest (absolute value) peak in the QRS complex; and (ii) the first positive peak in the QRS complex. It should be understood, that, in all the embodiments detailed herein, any of the above definitions may be used when extracting the cardiac R-R intervals. The procedure of extracting cardiac R-R intervals from the electrocardiogram signals is well known in the art and can be executed, either manually or automatically, e.g., by a data processor which, in one embodiment, can be associated with the medical apparatus which provides the signals.

Once, extracted, the cardiac R-R intervals are analyzed for the purpose of determining the heart rate variability. This can be done, for example, by obtaining a frequency decomposition of the cardiac R-R intervals (e.g., Fourier-Transform, wavelet transform, autoregressive methods, maximal entropy and the like), or by any other algorithm for analyzing a sequential database.

Typically, heart rate variability analysis includes the calculations of several characterizing parameters, such as, but not limited to, standard deviation of normal-to-normal beats (SDNN), low-frequency power (LF), high-frequency power (HF), a very-low-frequency power and any combination (e.g., ratio) of these parameters.

SDNN equals the square root of the total power of the spectral analysis and indicates parasympathetic activity. In coronary artery disease patients, for example, where there is a reduced parasympathetic activity, the SDNN is small.

The very-low, low- and high-frequency ranges of the frequency decomposition are associated with different physiological mechanisms. The very-low frequency range, which typically peaks at about 0.04 Hz, is mainly associated with thermoregulation, the low frequency range, which typically peaks at about 0.12 Hz, relates to the baro-receptors reflex and the high frequency range, which typically peaks at about 0.3 Hz relates to the respiratory cycle.

Thus, the LF parameter indicates both parasympathetic and sympathetic activity, the HF parameter reflects parasympathetic activity and the LF/HF ratio is typically used as an index of sympatho-vagal balance. When the heart function is reduced due to coronary occlusion, a reduced vagal activity is the first to be attenuated. Therefore the vagal activity can serve as an index for characterizing impairment in coronary arteries.

According to a preferred embodiment of the present invention the heart rate variability analysis is performed over short time intervals, typically from about 3 minutes to 5 about minutes, during the baseline of endothelial function, so as to obtain a sufficient indication of possible impairment in autonomic nervous system activity and the blood vessel function.

As used herein the term "about" refers to ±10%.

The endothelial function of blood vessels is affected, as stated, by NO release, which is attributed to local platelet aggregation, production of thrombin and release of serotonin and ADP. The response of the blood vessel when exposed to specific conditions and stimuli can serve as an indicator for rate of NO release. To this end see, Vita J A et al., "Patients with evidence of coronary endothelial dysfunction as assessed by acetylcholine infusion demonstrate marked increase in sensitivity to constrictor effects of catecholamines,", Circulation 1992, 85:1390-1397; Deanfield J E et al., "Silent myocardial ischemia due to mental stress," Lancet 1984, 2:1001-1005; Gage J E et al., "Vasoconstriction of stenotic coronary arteries during dynamic exercise in patients with classic angina pectoris: Reversibility by nitroglycerin," Circulation 1986, 73:865-876; Gordon J B et al., "Atherosclerosis and endothelial function influence the coronary response to exercise," J Clin Invest 1989, 83:1946-1952; Nabel E G et al., "Dilation of normal and constriction of atherosclerothic coronary arteries caused by cold pressor test," Circulation 1988, 77:43-52; Zeiher A M et al., "Coronary vasomotion in response to sympathetic stimulation in humans: Importance of the functional integrity of the endothelium," JACC 1989, 14:1181-90; Anderson E A et al., "Flow-mediated and reflex changes in large peripheral artery tone in humans," Circulation 1989, 79:93-100; and Corretti M C et al., "Correlation of cold pressure and flow-mediated brachial artery diameter responses with the presence of coronary artery disease," Am J Cardiol 1995, 75:783-787.

Hence, increased flow (hyperemia) and arterial diameter, which indirectly indicate normal release of nitric oxide and endothelial function, appear after a short occlusion (several minutes) and reopening of an artery.

Stimuli for myocardial ischemia such as exercise and exposure to cold are associated with adrenergic stimulation and increased circulating catecholamines. Such stimuli have been associated with absolute decrease in myocardial perfusion and epicardial constriction in patients with early and advanced coronary atherosclerosis.

The dilation of normal and the constricted sclerotic coronary arteries with a sympathetic stimulus (e.g., cold pressure testing), mirrors the response to the endothelium-dependent dilator acetylcholine. Such stimuli can cause constriction in large peripheral artery, even beyond the constriction caused by distal circulatory arrest. Thus, both peripheral and coronary arteries having reduced endothelial function are associated with increased sensitivity to constrictor effects of catecholamines.

Hence, according to a preferred embodiment of the present invention method 10 further comprises an optional step in which the blood vessel is stimulated, prior to the above measurements. It will be appreciated that a proper stimulus to the blood vessel can significantly enhance the accuracy of the measurement. For example, by determining the blood vessel characteristics after a stimulus which, in normal blood vessel, increases NO release, the physician or the nurse may gain information about the level of response of the blood vessel to that specific stimulus.

Many types of stimuli are contemplated, provided that these stimuli generate a detectable response of the blood vessel in terms of vasoactivity. Representative examples include, without limitation, mechanical stimuli, thermal stimuli, chemical stimuli, electrical stimuli and the like.

Mechanical stimulus may be, for example, an external pressure applied on the blood vessel, e.g., using a sphingomanometer, so as to temporarily occlude the blood flow therein. As stated, the response of a normal blood vessel to such occlusion is increased release of NO and endothelial function, which can be detected by measurement of the blood vessel characteristics and/or heart rate variability as further detailed hereinabove. Thermal stimulus may be, for example, a dramatic temperature decrease, typically to about 5-10 degrees centigrade which induces vasoconstriction. A chemical stimulus is preferably non invasive and may be a vasoactive agent, capable of altering the physiologic state of the blood vessel. A representative example of a chemical stimulus is nitroglycerin.

The type of stimulus or stimuli which is used preferably depends on (i) the blood vessel under determination, (ii) the overall medical condition of the subject and (iii) the probability that the subject is suffering from endothelial dysfunction. Other selection rules for the type of stimuli are also contemplated.

Figure 3:
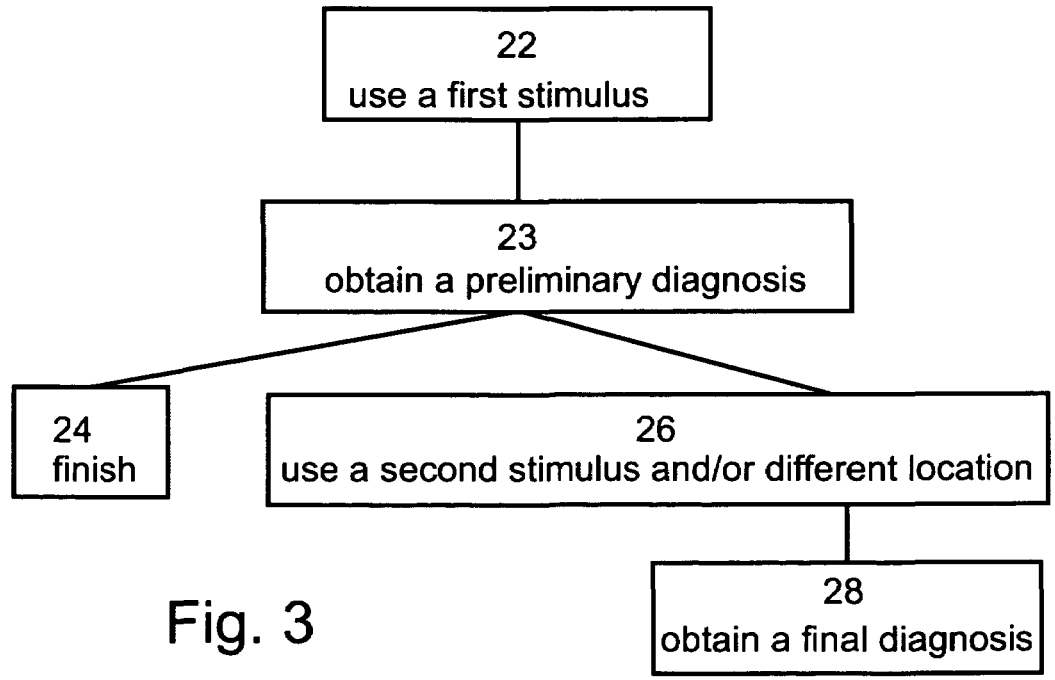
FIG. 3 is a flowchart diagram of another method of determining endothelial dependent vasoactivity of a subject, according to a preferred embodiment of the present invention.

A representative example of a determination protocol is illustrated in the flowchart diagram of FIG. 3. Hence, the determination protocol preferably include two phases, in which in a first phase, designated by Blocks 22-23, the blood vessel characteristics and the heart rate variability are determined under a first stimulus, thereby obtaining a preliminary diagnosis. The preliminary diagnosis can be characterized, e.g., using a correlation function which correlates between the different measurements. More specifically, the first phase of the determination protocol, allows to preliminary determine of both the level of endothelial dependent vasoactivity, and the level of autonomic nervous system activity. Based on the results of the first phase, a preliminary characterization of the probability that the subject is suffering from endothelial dysfunction can be obtained, using a two-valued index (V, A), where "V" stands for the level of endothelial dependent vasoactivity and "A" stands for the level autonomic nervous system activity. Depending on the two-valued index of the subject, the physician or the nurse can decide whether to finish the protocol (Block 24) or to perform an additional determination phase (Block 26), under other types of stimuli and/or at different locations on the subject's body. The additional determination phase is then preferably used for obtaining a final diagnosis (Block 28).

As a representative example, suppose that the first phase of the determination protocol is performed, under a mechanical stimulus, on the brachial and radial arteries of the subject, and that after the first phase it is possible to differentiate (i) whether the subject has a normal or an abnormal endothelial dependent vasoactivity, and (ii) whether the subject has a normal or an abnormal autonomic nervous system activity. Then, the respective two-valued index can have one of four combinations: (V="normal", A="normal"), (V="abnormal", A="normal"), (V="normal", A="abnormal") and (V="abnormal", A="abnormal"). One ordinarily skilled in the art will appreciate that the first combination and the fourth combination characterize, respectively subjects having the lowest and highest probabilities of suffering from endothelial dysfunction.

Subjects which are characterized by a combination other than (V="normal", A="normal") preferably undergo an additional phase of the determination protocol, which may be, for example, a thermal phase (e.g., a cold pressure test) where a thermal stimulus is applied to the brachial, radial and/or carotid arteries of the subjects.

According to a preferred embodiment of the present invention the thermal phase of the determination protocol can also comprise a continuous measurement of heart rate variability (e.g., using one ore more electrocardiogram leads) simultaneously with the pressure-related signals recording. Typically, this phase is performed in a temperature-controlled room, where the subject is exposed to a sequence of different temperatures during the examination. For example, the subject may be exposed to an alternating sequence of predetermined periods in which an exposure to a low temperature period is followed by a recovery period in which the subject the temperature is increased to a normal value. Typical temperature ranges are 0-15° C. for low temperature periods and 22-27° C. for recovery periods. The exposure to different temperatures may be done by any thermal mechanism capable of maintaining a substantially constant temperature for a predetermined period of time. Representative examples include, without limitations, a bath of liquid being in the desired temperature, and a thermal device being in the desired temperature and capable of surrounding an external organ of the subject. Such a thermal device may be in a form of a cuff containing fluid.

As will be appreciated by one ordinarily skilled in the art, many of the above parameters can be extracted during the thermal phase. For example one elapsed time parameter, referred to herein as $T_1$, may be extracted from the pulse transit time between the brachial and radial arteries. An additional elapsed time parameter referred to herein as $T_2$, is preferably extracted by measuring the transit time between peaks of the QRS complexes detected by the electrocardiogram lead and peaks of the pressure-related signals recorded of the carotid.

$T_2$ is the sum of two physiological periods: (i) the pre-ejection period, which is the time needed for the electrical activity of the heart to cause the iso-volumic contraction that leads to the opening of the aortic valve; and (ii) the valve-carotid period, which is the time needed for a pulse wave to move from the aortic valve to the measured location on the carotid. These two physiological periods are concomitantly shortened during the exposure to low temperatures. Normally, when the temperature starts to increase (e.g., during the recovery period of the above mention alternating sequence), the shortening of the pre-ejection period continues [Mezzacappa E S, et al., "Vagal Rebound and recovery from psychological stress," Psychosom Med 2002, 63:650-657] while the aortic-valve-carotid period begins to prolong. Thus, a comparison between the values of $T_2$ at different times can be used to characterize the endothelial activity.

More specifically, if during the recovery period, $T_2$ restores its typical baseline value the subject is diagnosed as having normal endothelial activity, because the increment of the valve-carotid period compensates the shortening of the pre-ejection period, which, as stated continues during recovery.

According to a preferred embodiment of the present invention the pulse wave amplitude is obtained from the same three arteries sites, i.e., brachial, radial and carotid arteries.

There are many advantages to this determination protocol. First, as the thermal stimulus is less comfortable to the subject, it is only performed on those subjects who are more likely to suffer from endothelial dysfunction.

Second, the second phase includes also measurements on the carotid thereby significantly increases the accuracy of the results. As will be appreciated, the carotid cannot be mechanically occluded, even for a short duration, without risking the subject. Thus the second phase preferably includes thermal stimulus so as to allow the measurement to be performed on the carotid.

Third, it is recognized that cold pressure vasoactivity, measured in brachial artery, correlates more closely with the presence of coronary artery disease than flow-mediated vasoactivity. Thus, the use of thermal stimulus on the brachial artery serves for further validation of the preliminary results.

Forth, although atherosclerosis in brachial arteries is significantly correlated with coronary artery disease, a stronger correlation was found to atherosclerosis in the carotid. The determination of the autonomic nervous system activity, in all three arteries serves as an additional validation which thereby increases the overall accuracy. The combination of two channels, in which in a first channel pressure-related signals are being analyzed for determining blood vessel characteristics, and in a second channel electrocardiogram signals are being analyzed to determine heart rate variability, contributes to increased interpretation accuracy of abnormal results obtained from both channels.

According to another aspect of the present invention, there is provided a system 30 for determining endothelial dependent vasoactivity of the subject. The system may be used for executing selected steps of method 10.

Figure 4:
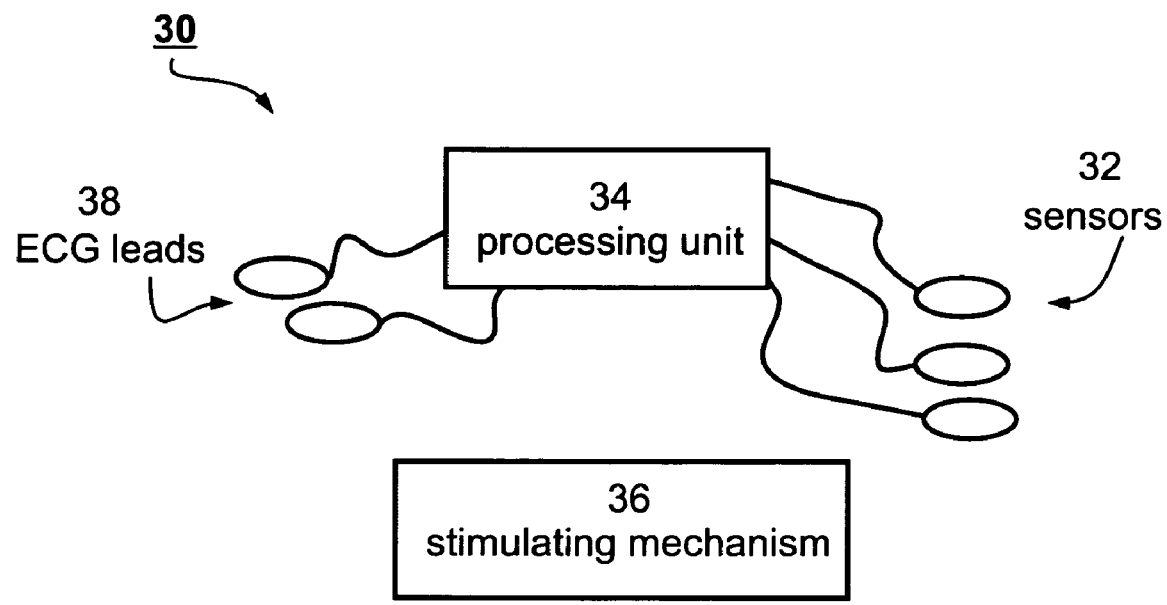
FIG. 4 is a schematic illustration of a system for determining endothelial dependent vasoactivity of the subject, according to a preferred embodiment of the present invention.

Referring now again to the drawings, FIG. 4 is a schematic illustration of system 30 which, in its basic configuration comprises an arrangement of sensors 32 for recording the pressure-related signals. According to a preferred embodiment of the present invention sensors 32 can be piezoelectric ceramic elements or membrane-based sensors, such as, but not limited to, electrate microphones. In use, sensors 32 are preferably positioned on several locations adjacent to one or more blood vessel.

System 30 further comprises a processing unit 34 which receives, records and processes the pressure-related signals, sensed by sensors 32. In addition unit 34 is programmed to extract parameter(s) from the pressure-related signals, and to use the parameter(s) for the purpose of determining a change of blood vessel characteristics and/or autonomic nervous system activity, as further detailed hereinabove.

According to a preferred embodiment of the present invention system 30 may further comprise a mechanism 36 for stimulating the blood vessel. Mechanism 36 is preferably capable of stimulating the blood vessel in any of the above types stimuli, hence can be a mechanical, thermal, electrical mechanism or chemical mechanism. Additionally, mechanism 36 can be a mechanism for generating mental stress or a device for allowing the subject to perform physical exercise. For example, for mechanical stimulus, mechanism 36 can comprise a sphingomanometer, for thermal stimulus mechanism 36 can be realized as a low temperature room or a bath of cold fluid, for electrical stimulus mechanism 36 can comprise electrodes, for chemical stimulus mechanism 36 may be a vasoactive agent, and the like.

As stated, the present invention also contemplates the determination of an autonomic nervous system activity, e.g., by heart rate variability analysis. Thus, according to a preferred embodiment of the present invention system 30 further comprising one or more electrocardiogram leads 38 being for sensing electrical signals of the chest of the subject. In this embodiment, processing unit 34 (or an additional processing unit) calculates heart rate variability from the electrocardiogram signals sensed leads 28, as further detailed hereinabove.

As further demonstrated in the Example section that follows, the present invention provides cost effective system and method. A typical examination period for an individual subject is relatively short (from about 5 minutes to about 30 minutes) and can be executed by paramedical staff, without the supervision of specialist medical staff. Preferably, the examination results are automatically analyzed, hence quickly providing general practitioners, cardiologists or internal medicine specialists with accurate and reliable information. The present invention can be routinely used for screening and diagnosis of large population and to differentiate between subjects in different stages and combinations of endothelial and coronary artery dysfunction.

It is expected that during the life of this patent many relevant technologies for recording signals near blood vessels will be developed and the scope of the term pressure-related signals is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

First Prototype System

A first prototype system has been designed and constructed. The system included (i) transducers and an amplifier, designed and assembled for the research; (ii) a processing unit (desktop computer, Pentium IV); (iii) an A/D sampling card, purchased from National Instruments DAQ NI-488.2; (iv) data acquisition software, purchased from National Instruments™ Labview 5.1.1™, custom designed; and (v) data analysis software, purchased from Matlab™, custom designed.

Figure 5:
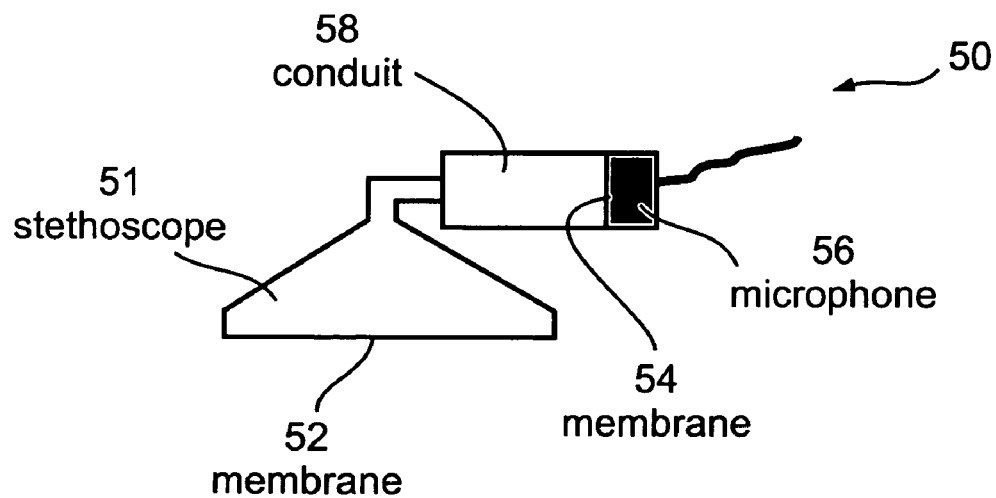
FIG. 5 is a schematic illustration of a transducer for sensing and transmitting the pressure-related signals, according to a preferred embodiment of the present invention.

FIG. 5 is a schematic illustration of a transducer 50. Transducer 50 included an electrate microphone 56 and a stethoscope 51. Transducer 50 was capable of detecting small movements of the subject's skin generated by the blood pulse wave passing thereunder. Microphone 56 was connected to stethoscope 51 by a short conduit 58, allowing a communication between a membrane 52 of stethoscope 51 and a membrane 54 of microphone 56. In use, a blood pulse wave passing under the skin generates vibrations in membrane 52, which are transmitted by conduit 58 to membrane 54, thus creating an electrical signal in microphone 56.

Figure 6:
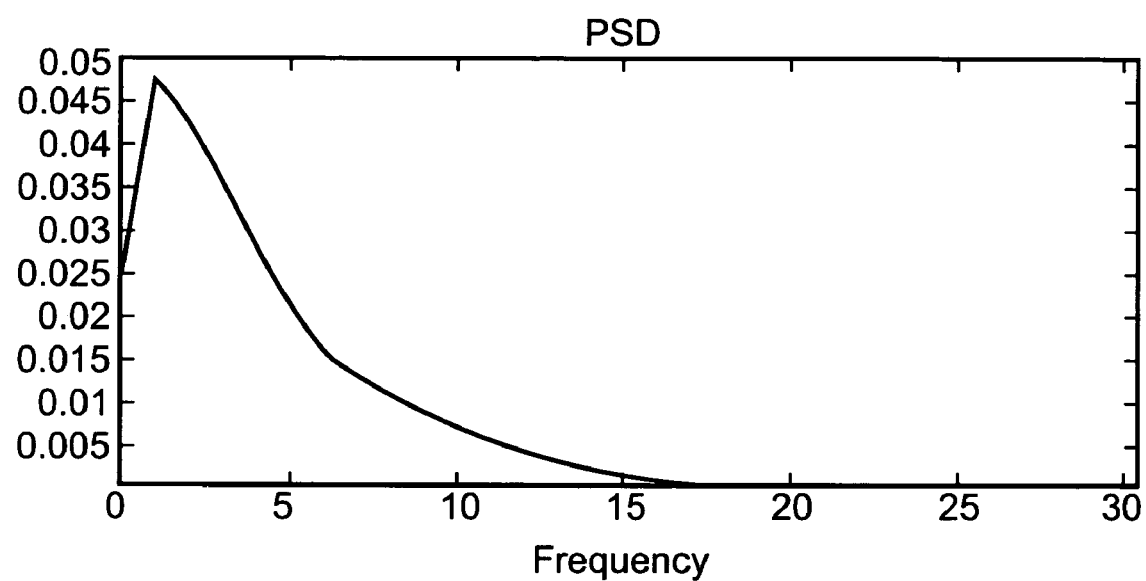
FIG. 6 shows a transducer's response to an input signal of about 1 Hz.

FIG. 6 shows the response of the transducer 50 to an input signal of approximately 1 Hz, obtained by physically oscillating the microphones. Note that although in its origin a typical stethoscope is designed to detect frequencies above 20 Hz, in practice the sensitivity range of transducer 50 is larger. Specifically, transducer 50 is capable of sensing low frequencies oscillatory motion.

The sampling rate of the data acquisition software was chosen to be 1000 Hz. This sampling rate provided the necessary precision for calculating the elapsed time between two successive pulses. Other sampling frequencies were tested and found less effective (higher frequencies demanded more memory and improvement in accuracy was negligible).

Figure 7:
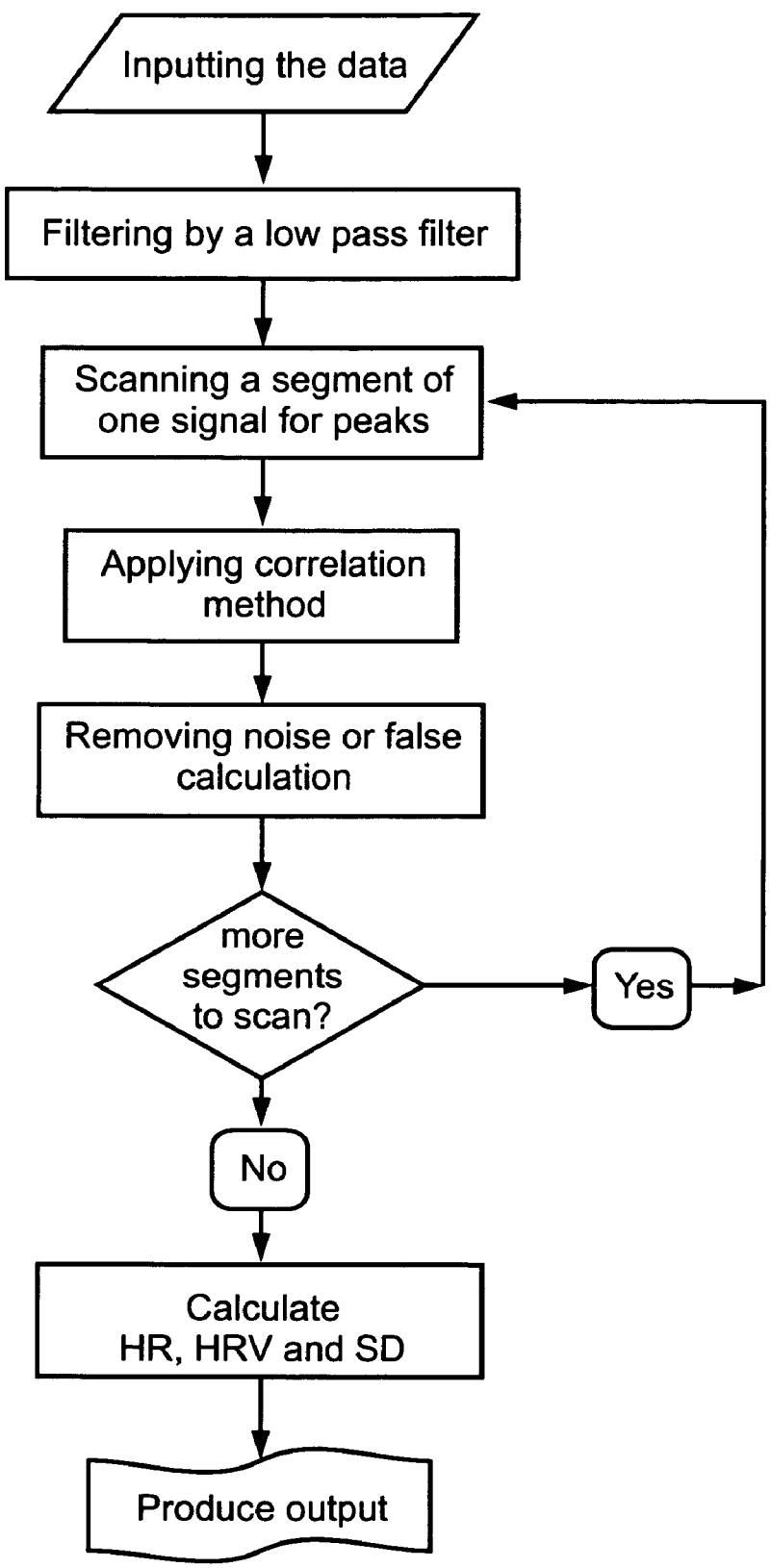
FIG. 7 is a flowchart diagram of a data analysis procedure, according to a preferred embodiment of the present invention.

FIG. 7 is a detailed flowchart diagram of the data analysis procedure. Hence, the raw data, as recorded using the transducers from two locations of the subject's body was loaded from the data acquisition software and filtered by a low pass filter (15 Hz). The data was in a form of a plurality of 10 seconds segments. Each segment was scanned for its peaks.

Peaks were defined by a zero derivative and were accepted for calculation if the following conditions were met: (i) the value of the peak was above a predetermined threshold, selected to be 70% of the average maximum value; and (ii) the time interval between the peak and its former peak (of the same location) was more than 0.25 seconds.

Using a correlation method, the elapsed time between two appropriate peaks from two different locations of the body was measured. Mean value and the standard deviation of the elapsed time was calculated, so as to eliminate unreasonable results (originated from noise, movement of the subject, erroneous calculation etc.). The standard deviation acceptance range was about 10%. This process was repeated for all the peaks of all the segments.

The accepted peaks were used for calculating heart rate, heart rate variability and standard deviation (respectively designated in FIG. 7 by HR, HRV and SD). The heart rate was defined as the time between successive peaks of the same location. The heart rate variability was obtained by calculating the standard deviation of the heart rate in each segment. The heart rate variability was averaged over all the accepted segments and a standard deviation of the heart rate variability was obtained. A graphical output of the results was produced in the final step.

Figure 8A:
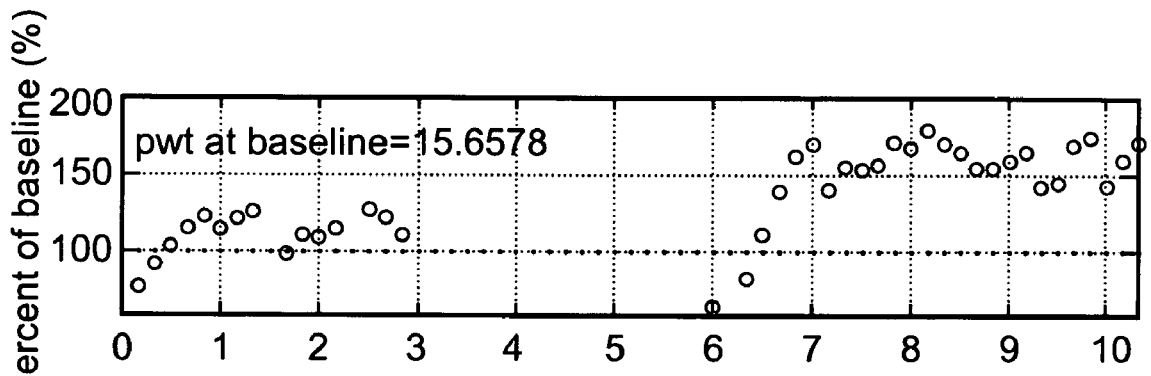
FIGS. 8a-c are representative graphical outputs of the procedure of FIG. 7.
Figure 8B:
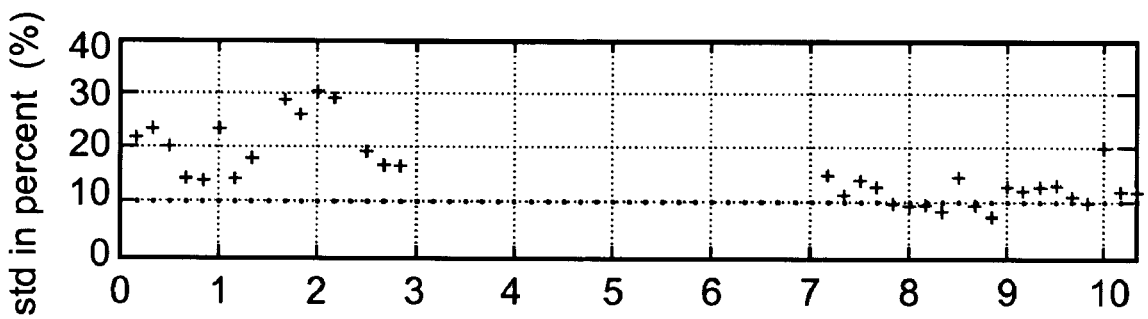
Figure 8C:
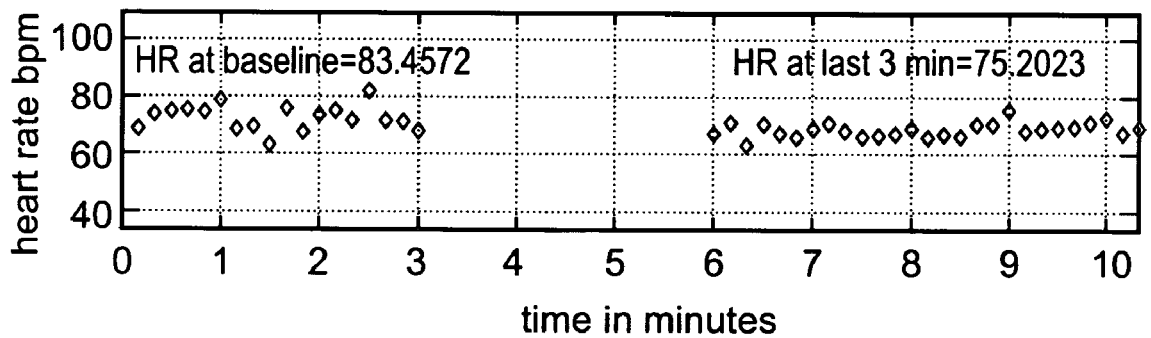

FIGS. 8a-c are representative graphical output of the procedure. FIG. 8a shows the relative change in elapsed time between the two transducers in % designated PWT (pulse-wave time parameter), as a function of time in minutes. Each point represents an average of approximately 10 seconds. The average value of PWT during the first three minutes of baseline is presented numerically; the dotted line represents the relative average value of baseline.

FIG. 8b shows the percentage of the standard deviation of PWT calculated for the points represented in FIG. 8a. High standard deviation during baseline represents movements of the subject or a noisy recording.

FIG. 8c shows the heart rate as a function of time. Each point represents an average of approximately 10 seconds. Numerical values of heart rate are presented (designated HR in FIG. 8c).

Example 2

In Vivo Measurements Using the First Prototype System

In vivo tests were performed on 21 volunteers, using the first prototype system of Example 1. Two transducers were connected to the subject under examination. A first transducer was connected to the radial artery at the wrist, and a second transducer was connected to the brachial artery about 5-10 cm above the elbow on the proximal side of the arm. The transducers were fastened with a cuff inflated to a pressure of 20 mmHg, so as to improve that signal to noise ratio, and to prevent partial occlusion of the vessel. An additional cuff, purchased from Hokanson, US, was positioned above the first cuff, for the purpose of implementing ischemia (mechanical stimulus).

Mechanical Stimulus

Subjects were tested at different hours of the day without fasting. Each subject was in a sitting posture in a temperature-controlled room (18° C.-24° C.). The examination of each subject included: (i) three minutes of baseline recording (without stimulus); (ii) three minutes of induced ischemia in the brachial artery (using the additional cuff); and (iii) five minutes of recording during recovery subsequently to cuff release.

Thermal Stimulus

Vasoconstriction was induced by submerging the right hand in cold water (8° C.), during continuous recording from the left hand in a sitting position. The subjects also underwent relaxation periods in which the right hand was in water at room temperature (21° C.).

The examination of each subject included: (i) a few minutes in water in room temperature; (ii) three minutes of baseline recording (room temperature); (iii) one minute of vasoconstriction (cold water); (iv) three minutes of room temperature; (v) two minutes of vasoconstriction; (vi) at least three minutes of recovery in room temperature.

Combined Stimuli

Several factors, such as temperature, food, drugs, physical exercise before examination and sympathetic stimuli, can affect vasomotor activity. In the above tests, it has been observed, that in some cases, examined individuals who were supposed to be with normal endothelium dependent vasoreactivity had different responses to reactive hyperemia at subsequent examinations. It was also found that these changes were in correlation with the elapsed time parameter measured in baseline. When the elapsed time parameter during baseline was relatively high (above 40-42 ms) the subject's response to reactive hyperemia was weak or completely absent. When the elapsed time parameter during baseline was lower (20-40 ms) the subjects' response to reactive hyperemia was normal. This implied that there is a "physiological window" in which the system produces the most reliable results.

Hence, the following standard procedure was developed to increase the probability that examinations were performed within the "physiological window": (i) subjects were examined after fasting for 6-8 hours; (ii) the examination was performed in a quiet temperature controlled room (18° C.-20° C.); (ii) after three minute recording the subject was disconnected from the transducers, walked moderately for two minutes and returned to a sitting position, so as to enhance sympathetic activity, reduce the elapsed time parameter and induce relaxation; (v) two subsequent examinations under mechanical stimulus as described above, with a 10-minute rest between the examinations to allow full recovery of the artery.

Under this protocol, an impaired endothelial function has been diagnosed only in cases where both examinations showed abnormal endothelium dependent vasoreactivity.

Comparative Study

The results obtained by the first prototype system of Example 1 were compared to results obtained using a high-resolution ultrasonography device (HP sonos 5500). Each subject underwent a first examination using the ultrasonography device and a second examination using the prototype system, with 30 minutes rest between the tests. All subjects were examined after fasting for 8 hours without smoking or coffee.

The ultrasonography examination of each subject included: (i) three minutes baseline recordings; (ii) three minutes of brachial artery occlusion; and (iii) ten minutes of recovery with continuous recording.

For each subject, 4 artery diameters, designated $D_1$-$D_4$, were calculated off line from the ultrasound images: $D_1$, calculated during baseline phase, 1 minute from start; $D_2$, calculated during baseline phase, 2 minutes from start; $D_3$, calculated during cuff phase, 1 minute after deflation, and $D_4$, calculated during cuff phase 1.5 minutes after deflation.

The baseline diameter is defined as the average between $D_1$ and $D_2$ and the absolute diameter change is defined as the subtraction of $D_4$ from the baseline diameter. Specifically:

$$\text{baseline} = \frac{D_1 + D_2}{2} \quad \text{(EQ. 3)}$$

$$FMD\% = 100 \cdot \frac{D_4 - \text{baseline}}{\text{baseline}} \quad \text{(EQ. 4)}$$

where FMD is abbreviation for Flow Mediated Dilatation. Typical FMD measurements are from about −6.2% to about +31.8%. Abnormal FMD was defined when the FMD value was below +6%.

Figure 9A:
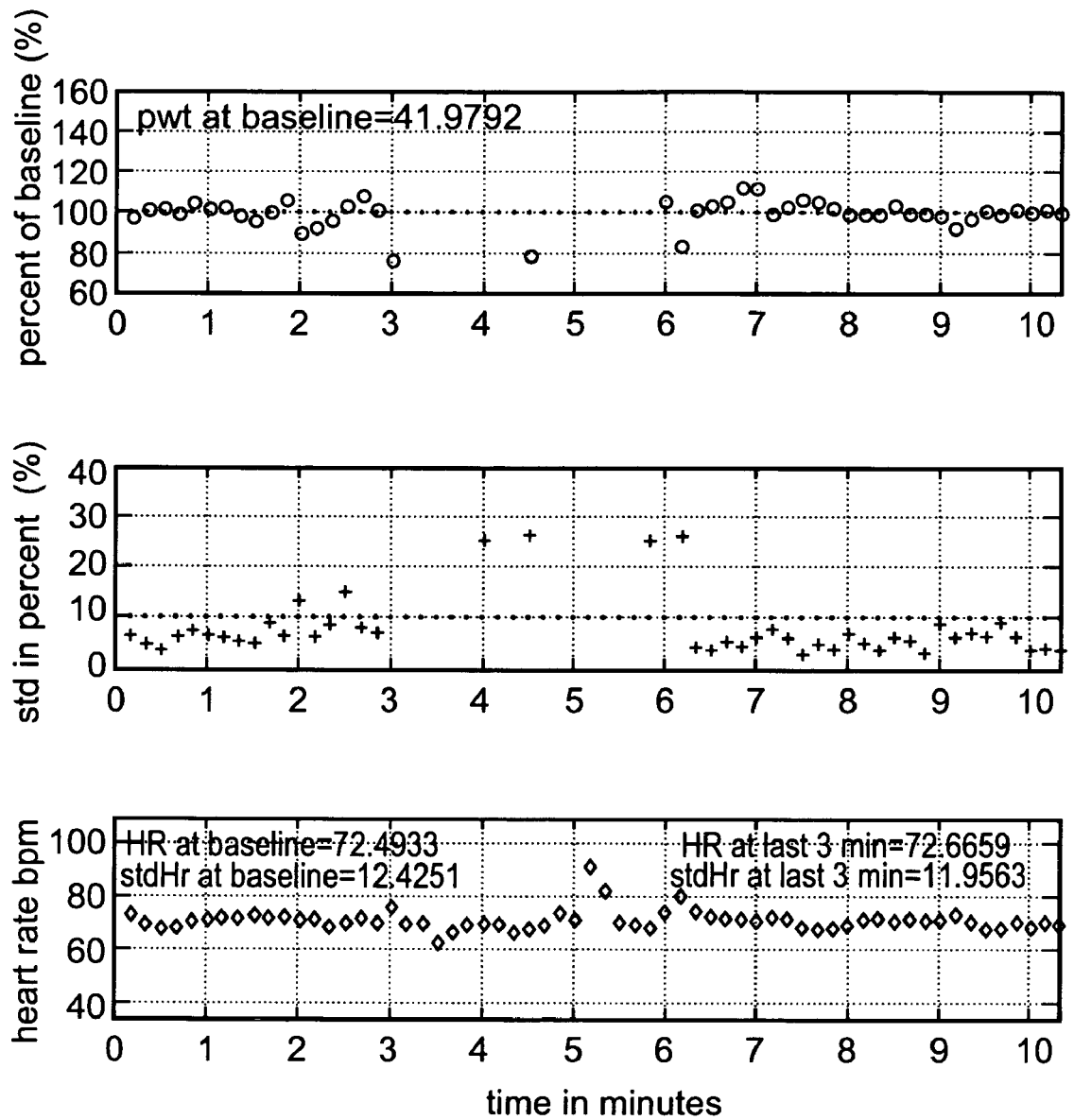
FIGS. 9a-e shows output of a comparative examination, which included a combined stimuli protocol, according to a preferred embodiment of the present invention.
Figure 9B:
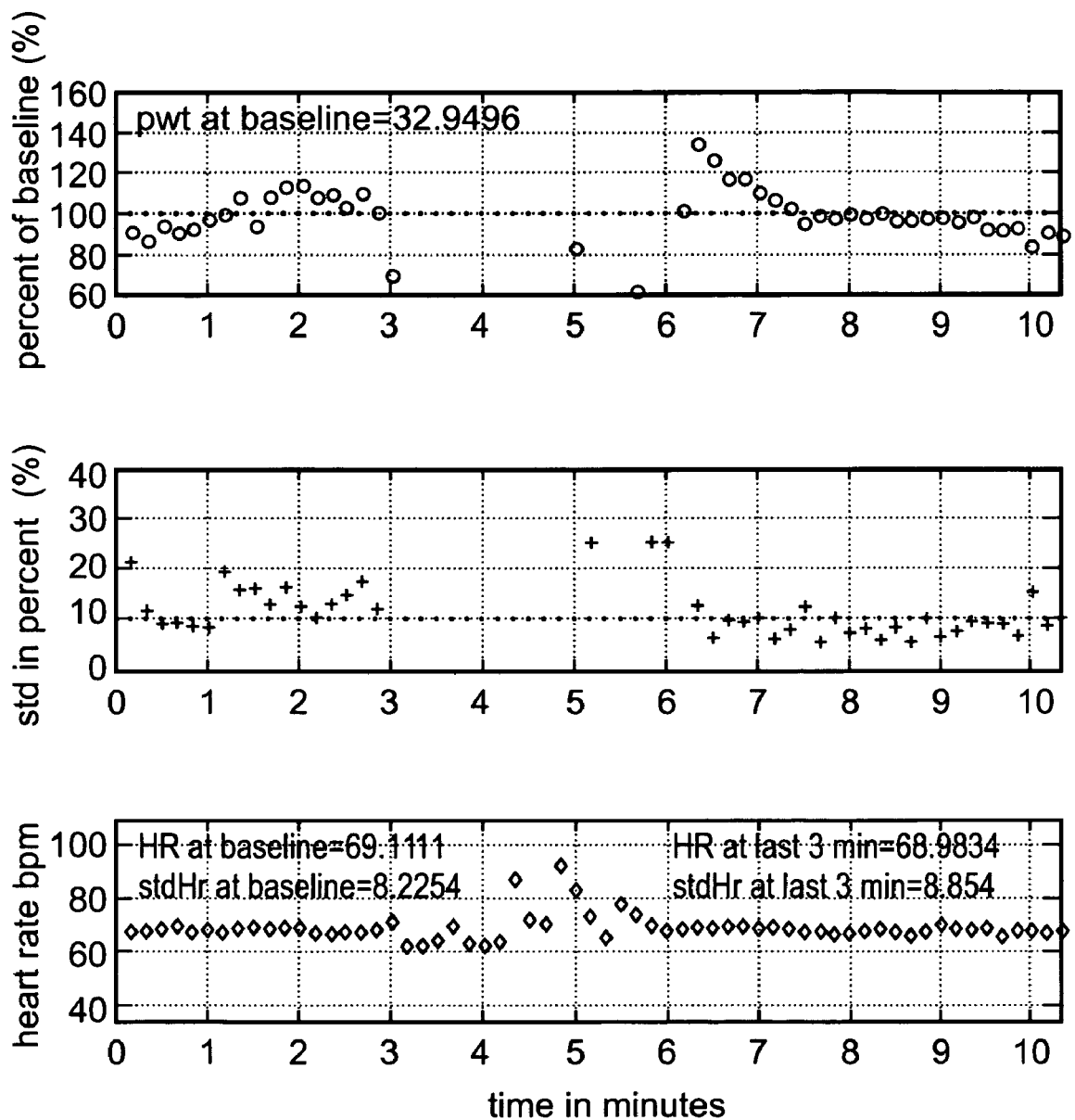
Figure 9C:
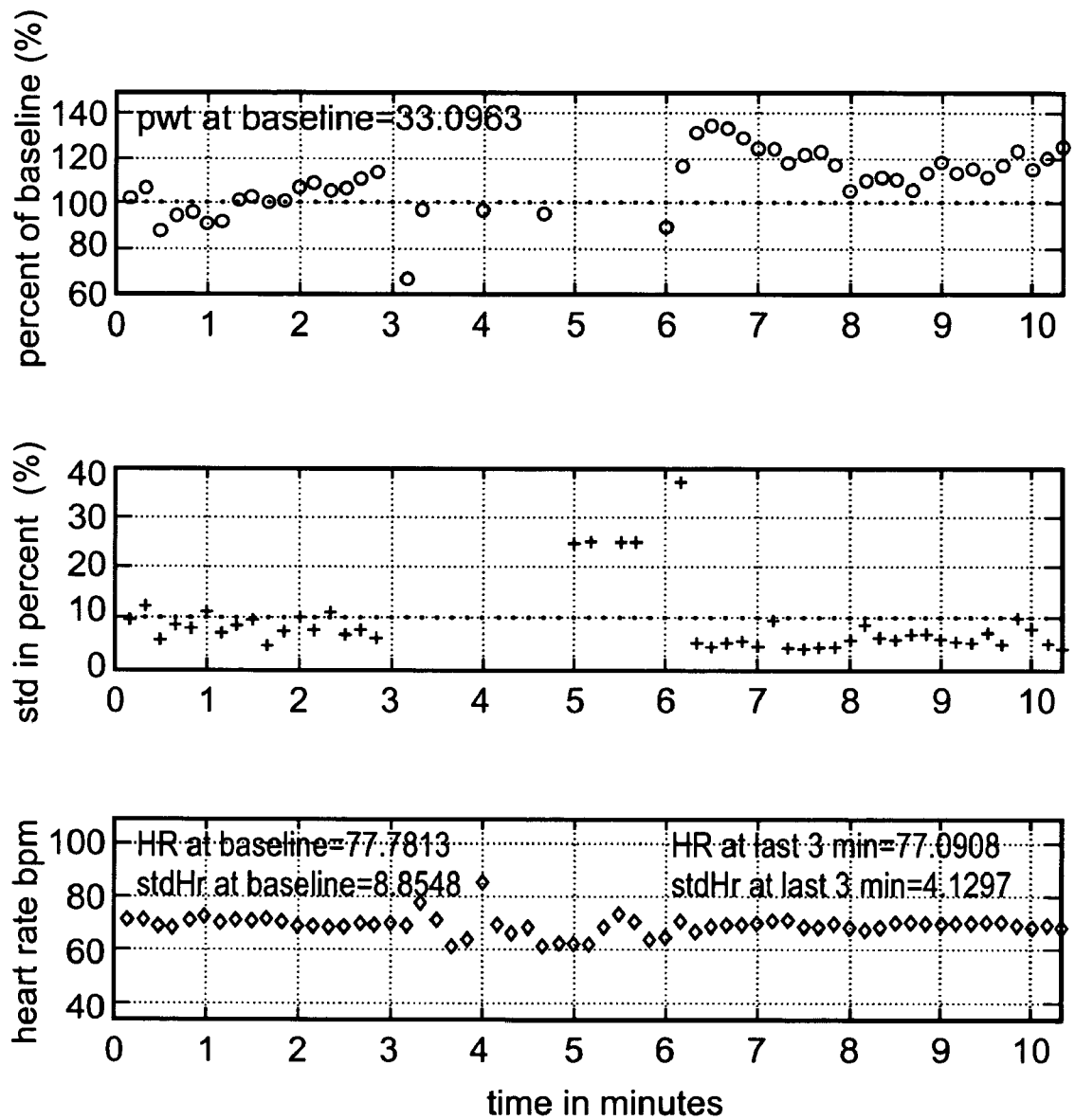
Figure 9D:
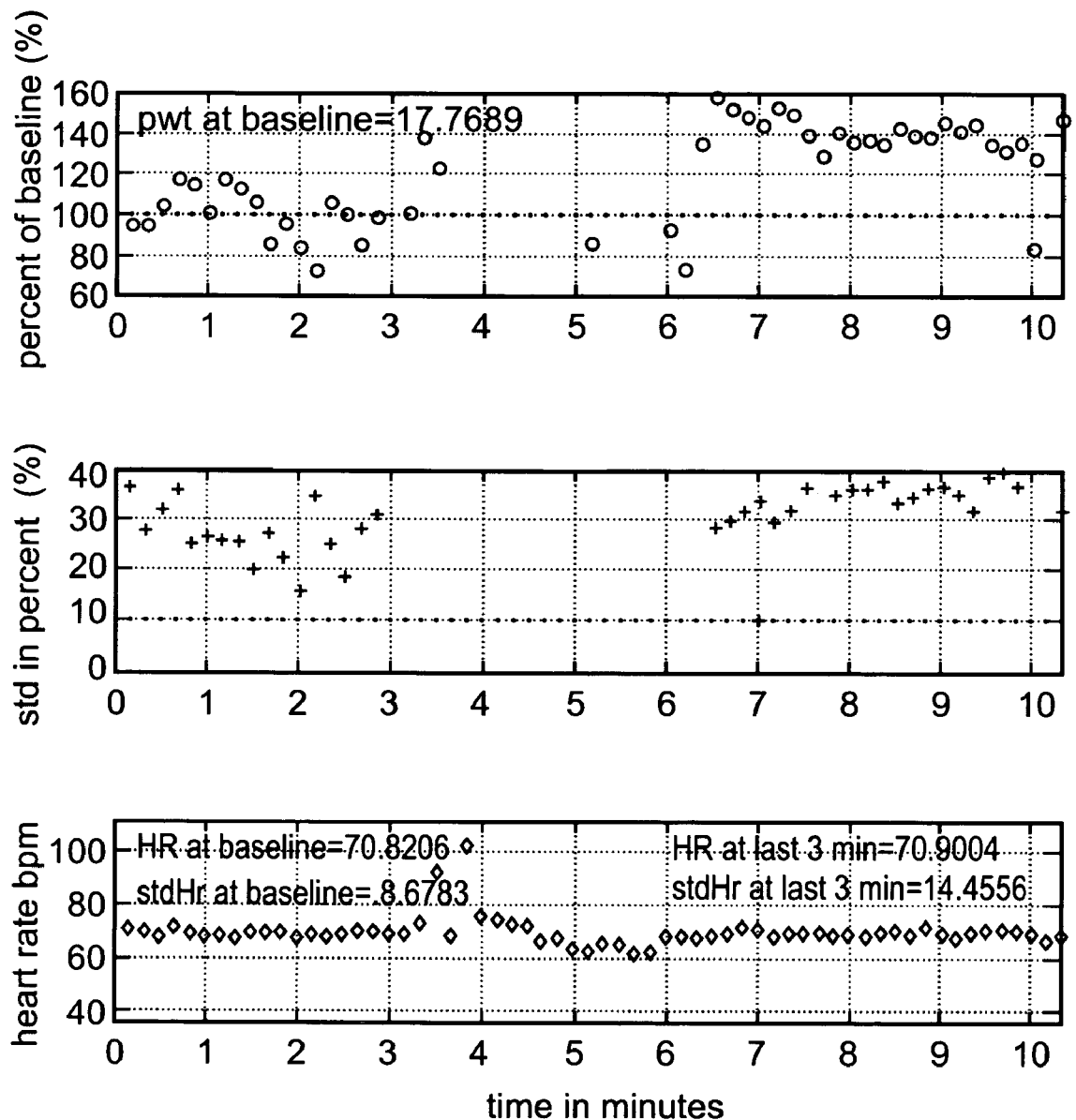
Figure 9E:
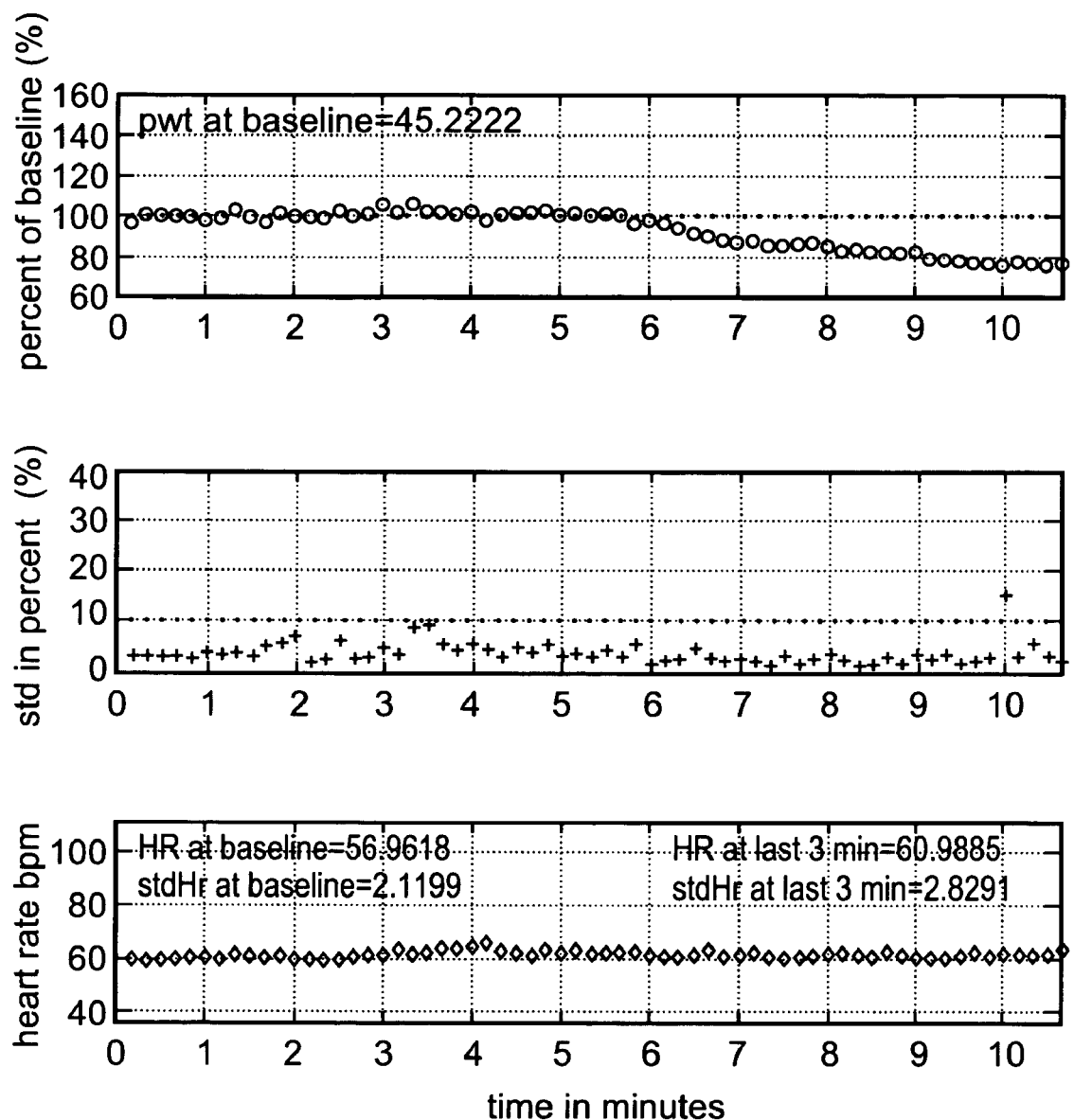

The prototype system examination of each subject included the combined stimuli protocol as further detailed above. The output of this examination is shown in FIGS. 9a-e. FIGS. 9a-b show examples of the output obtained for individuals with abnormal endothelial activity, FIGS. 9c-d show examples of the output obtained for individuals with normal endothelial activity, and FIG. 9e is an example of an output in which the elapsed time decreases while the arterial diameter is increasing as a result of nitroglycerin intake in a lying posture. Each Figure shows PWT, the percentage of the standard deviation of PWT and the heart rate as a function of time, as further explained hereinabove (see description of FIGS. 8a-c).

Further details of the output presented in FIGS. 9a-e is summarized in Table 1, below.

TABLE 1

| Type of response | Maximum change in PWT after cuff release [%] | Response duration, T, after cuff release | EDV function |
| --- | --- | --- | --- |
| None | $\Delta(PWT) \approx 0$ | — | Abnormal |
| Weak | $\Delta(PWT) < 10$ | T < 2 min | Abnormal |
| Normal | $10 < \Delta(PWT) < 20$ | 2 < T > 4 | Normal |
| Strong | $\Delta(PWT) > 20$ | T > 4 | Normal |
| Negative | below baseline | — | — |

Results

Tables 2-3, below show the results obtained in the mechanical stimulus examination, where Table 2 shows the results obtained for low risk subjects and Table 3 shows the results obtained for high risk subjects.

TABLE 2

| Subject | | | Risk Factors | | | | | | PWT at baseline | | |
| --- | --- | --- | --- | --- | --- | --- | --- | --- | --- | --- | --- |
| No | Gender | Age | Gender | Age | Smoker | Hypertension | Cholesterol | Diabetes | [ms] | Response | Result |
| 1 | M | 39 | + | − | − | − | − | − | 30 | Strong | N |
| 2 | F | 19.5 | − | − | − | − | − | − | 42 | Normal | N |
| 3 | F | 32 | − | − | − | − | − | − | 51 | Normal | N |
| 4 | M | 26 | + | − | − | − | − | − | 32 | Normal | N |
| 5 | F | 42 | + | − | − | − | − | − | 21-33 | Normal | N |
| 6● | F | 71 | − | + | − | − | − | − | 55 | None | AN |
| 7 | F | 50 | − | − | + | − | − | − | 58 | Strong | N |
| 8◊ | F | 24 | − | − | + | − | − | − | 20 | Strong | N |

TABLE 2-continued

| Subject | | | Risk Factors | | | | | | PWT at baseline | | |
|---|---|---|---|---|---|---|---|---|---|---|---|
| No | Gender | Age | Gender | Age | Smoker | Hypertension | Cholesterol | Diabetes | [ms] | Response | Result |
| 9 | F | 28 | − | − | − | − | − | − | 52 | Weak | N |
| 10 | F | 26 | − | − | − | − | − | − | 44 | Weak(−) | AN |

N = Normal; AN = Abnormal; (−) = Negative
● had a continuous trembling in hands
◇ smokes 5 cigarettes a day.

TABLE 3

| Subject | | | Risk Factors | | | | | | PWT | | | Clinical |
|---|---|---|---|---|---|---|---|---|---|---|---|---|
| No | Gender | Age | Gender | Age | Smoker | Hypertension | Cholesterol | Diabetes | [ms] | Response | Result | comments |
| 1 | M | 56 | + | + | − | − | − | − | 33 | Normal | N | Regulates cholesterol with simovil |
| 2 | F | 54 | − | + | + | − | − | − | 48 | None | AN | |
| 3 | F | 52 | − | − | + | + | − | − | 53 | None | AN | Takes medication for Hyper-tension |
| 4 | M | 59 | + | + | + | − | − | − | 27 | None | AN | Smokes 10 cigarettes a day |
| 5 | M | 49 | + | + | + | + | − | − | 59 | None | AN | |
| 6 | M | 65 | + | + | − | − | + | − | 40 | None | AN | Receives medication for cholesterol |
| 7 | F | 54 | − | + | + | − | − | − | 65 | None | AN | |
| 8 | M | 54 | + | + | + | − | − | − | 48 | None | AN | |
| 9 | M | 63 | + | + | − | − | − | − | 28 | Negative | AN | CAD, orifice |
| 10 | F | 53 | − | + | + | − | − | − | 26 | Negative | AN | |
| 11 | F | 50 | − | − | + | − | + | − | 27 | Weak | N | |

N = Normal; AN = Abnormal

The results of Tables 2-3 are summarized in Table 4, below:

TABLE 4

| Population | age | n | Normal EDV | % | Abnormal EDV | % |
|---|---|---|---|---|---|---|
| High risk | 55.3 | 11 | 2/11[(1)] | 18% | 9 | 82% |
| Low risk | 37 | 10 | 8/10 | 80% | 2 | 20% |

[(1)] $p < 0.002$ high Vs low risk group

The average age of the groups with normal endothelium dependent vasoreactivity was 36.7±12.5 years and with abnormal endothelium dependent vasoreactivity was the 54.5±11.5 (p<0.01). The average elapsed time of baseline was 37.2±12.7 ms for the normal group and 44.8±13.3 ms for the abnormal group (P=0.1).

Figure 10A:
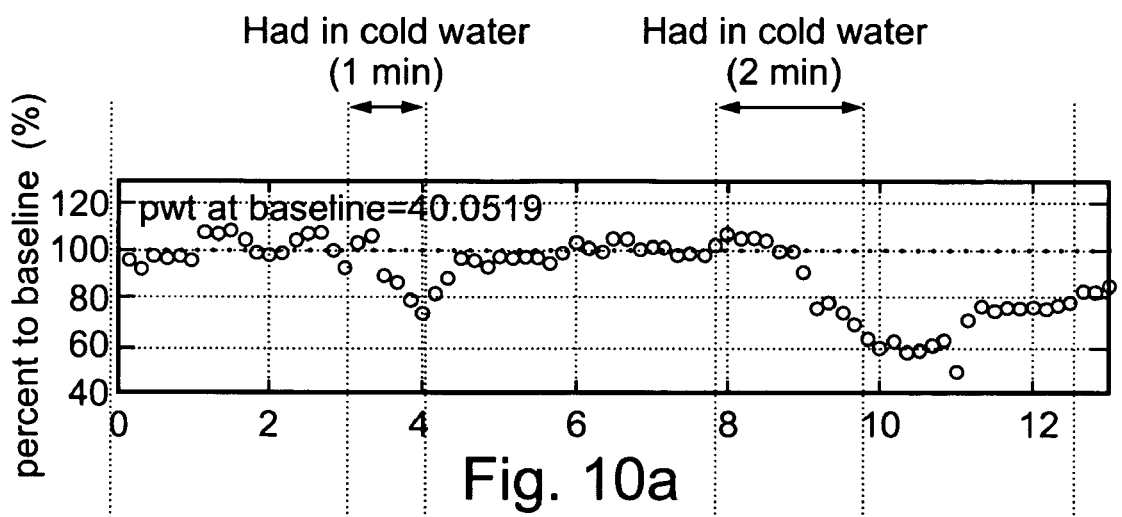
FIGS. 10a-c show relative changes in the elapsed time, standard deviation and heart rate variability, of one subject examined in a thermal stimulus test, according to a preferred embodiment of the present invention.
Figure 10B:
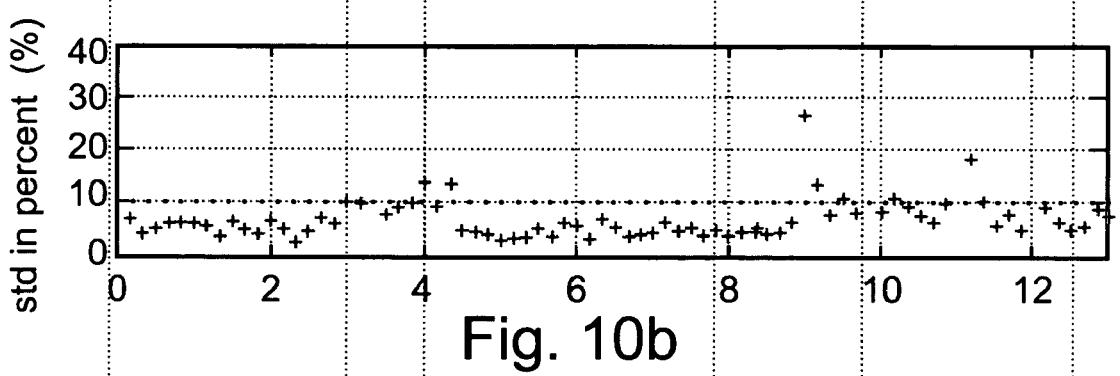
Figure 10C:
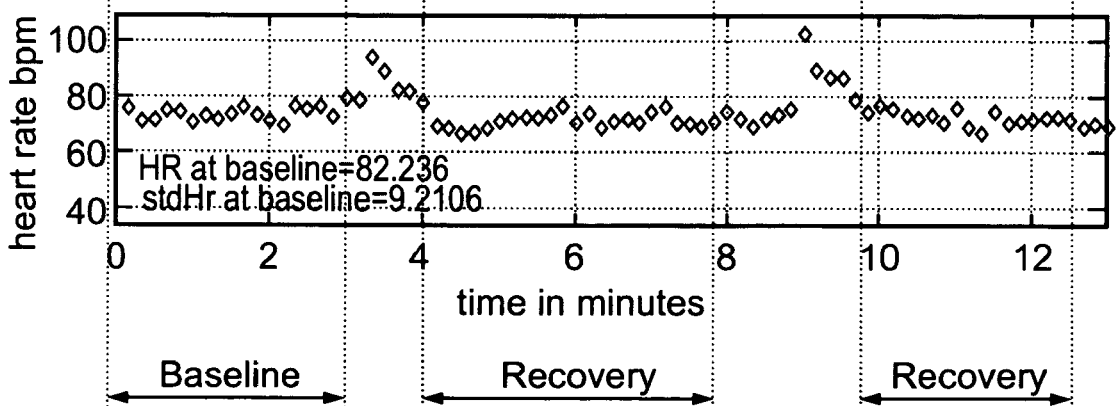

FIGS. 10a-c show relative changes in the elapsed time, standard deviation and heart rate variability, of one subject examined in the thermal stimulus test.

During the first three minutes, the elapsed time was measured and the average was calculated (the dotted line in FIG. 10a). When the right hand was submerged in cold water for 1 minute the elapsed time (measured on left hand) decreased almost linearly until it reached its lowest value (~70%). Heart rate increased substantially when the right hand was submerged in the cold water (FIG. 10c). When the right hand was pulled out of the cold water and submerged in room temperature water, the elapsed time increases almost linearly until the initial elapsed time value reached (recovery). When the right hand was submerged again for 2 minutes in the cold water, the elapsed time decreased to a minimum of ~60% from the initial baseline and heart rate was increased. Again, when right hand was pulled out of cold water and placed in room temperature water, the elapsed time raised again but did not reach initial baseline level until the examination has terminated.

Table 5 below shows the results of relative change in elapsed time for 6 subjects exposed to cold water.

TABLE 5

| No | Baseline 100% | [(1)] 1-minute submergence: PWT relative to baseline | recovery time (minutes) | Baseline 100% | [(2)] 2-minute submergence: PWT relative to baseline | [(3)] recovery time (minutes) |
|---|---|---|---|---|---|---|
| 1 | 100% | 70% | 1 | 100% | 40% | 2 |
| 2 | 100% | 70% | 4 | 100% | 40% | above 6 |
| 3 | 100% | 85% | 2 | 100% | 20% | 3 |

TABLE 5-continued

| No | Baseline 100% | (1) 1-minute submergence: PWT relative to baseline | recovery time (minutes) | Baseline 100% | (2) 2-minute submergence: PWT relative to baseline | (3) recovery time (minutes) |
|---|---|---|---|---|---|---|
| 4 | 100% | 80% | 1 | 100% | 30% | above 6 |
| 5 | 100% | 80% | 1 | 100% | 25% | 2.5 |
| 6 | 100% | 75% | 1.5 | 100% | 25% | 1.5 |
| Av. | 100% | 76.6 ± 6.0% | 1.75 ± 1.2 | 100% | 30 ± 8.3% | 3.5 ± 2.0 |

(1) $p < 0.001$ between control and 1 minute submergence.
(2) $p < 2.5E - 6$ between control and 2 minutes submergence.
(3) $p < 0.05$ between recovery time of 1 Vs 2 minutes submergence.

As can be seen from Table 5, a decline in elapsed time was found when the subject's hand was submerged in cold water. It can be seen that the change in the 2 minutes submergence relative to the 1 minute submergence is larger and recovery time is longer.

Figure 11A:
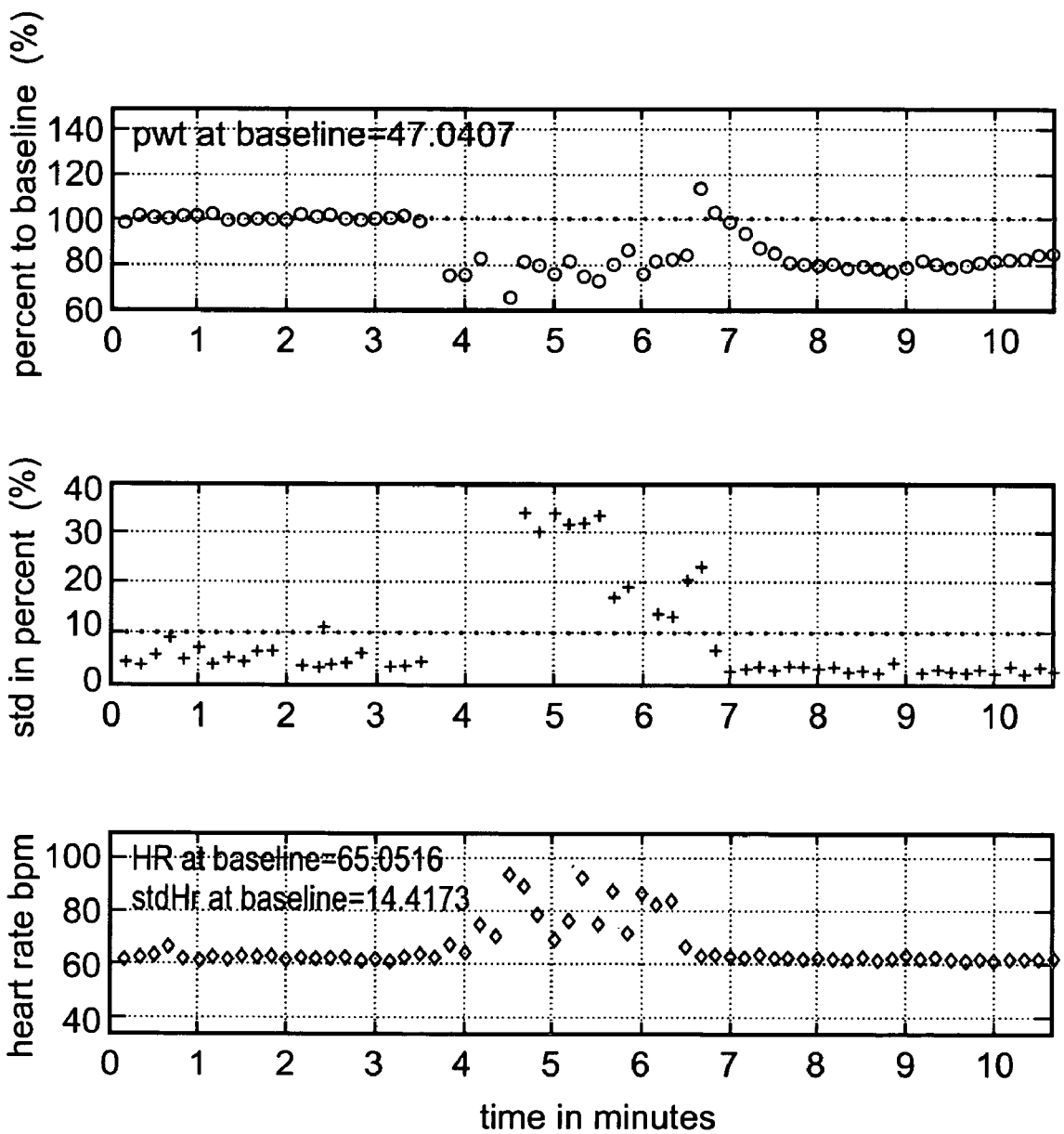
FIGS. 11a-b show the effect of lying posture on the elapsed time and the measurement of endothelium dependent vasoreactivity during treatment with nitroglycerin.
Figure 11B:
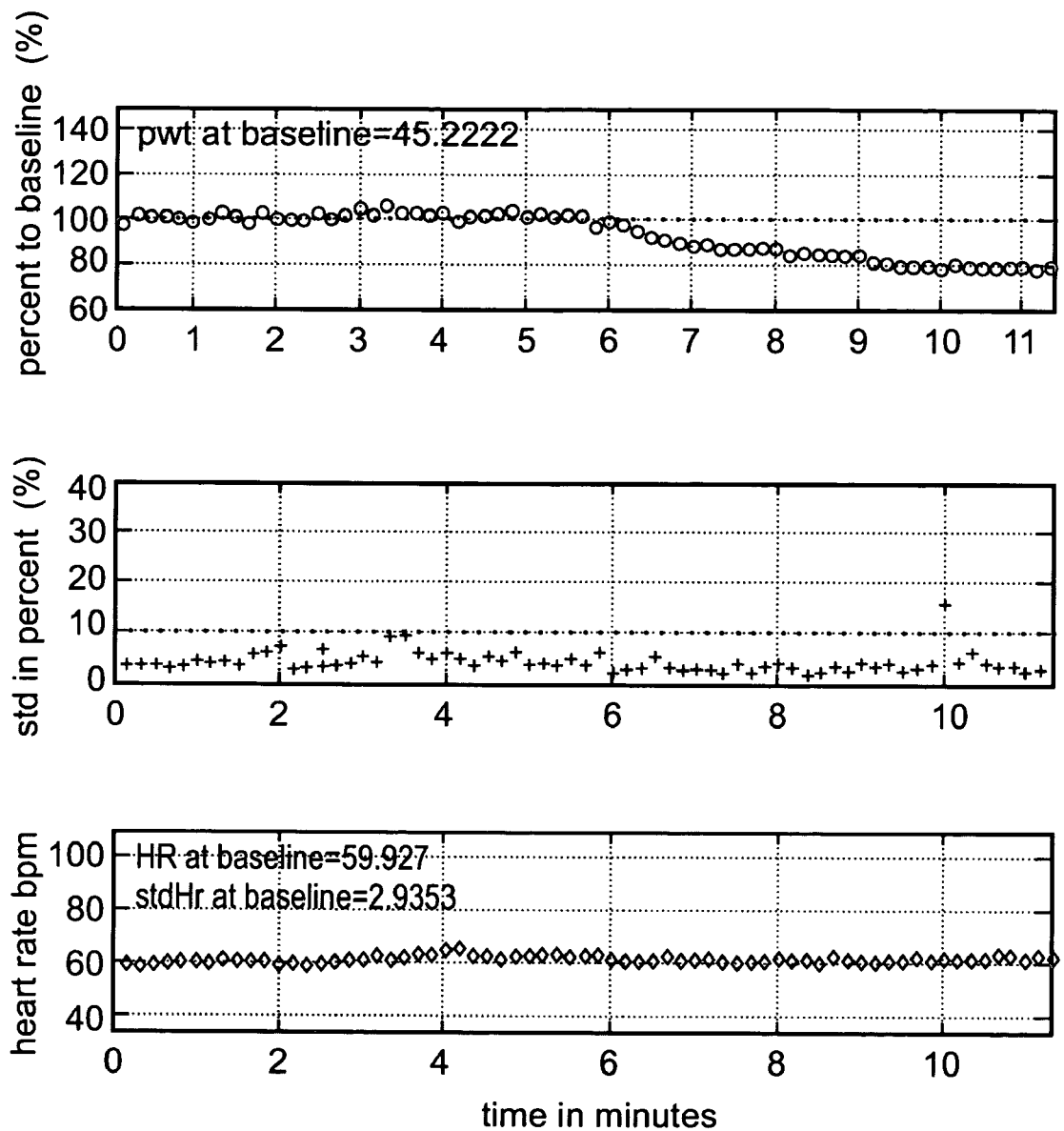

FIGS. 11a-b show the effect of posture on the elapsed time and the measurement of endothelium dependent vasoreactivity. Two individuals were examined with nitroglycerin while they were postured in a lying position for comparison with the ultrasonography examination. In these two examinations, the prototype system indicated abnormal response while the ultrasonography examination indicated normal response of increased hyperemia to nitroglycerine intake.

In order to look for a possible explanation to the different responses between ultrasonography examination and the prototype system, three other individuals were examined in two different postures, sitting and lying, at the same circumstances. The results are summarized in Table 6, below.

TABLE 6

| Subject | Posture | PWT at baseline [ms] | Type of response |
|---|---|---|---|
| 1 | Lying | 40 | Negative |
|   | Sitting | 26 | Normal |
| 2 | Lying | 47 | Negative |
|   | Sitting | 38 | Normal |
| 3 | Lying | 45 | Negative |
|   | Sitting | 41 | Normal |

As can be seen from Table 6, in these cases the response was negative for lying and normal for sitting. For the three individuals that where examined in both postures, the average elapsed time during baseline was higher in the examinations performed in a lying posture than in sitting posture. The results obtained may imply that above a certain threshold of the elapsed time during baseline, the ability of the prototype system to perform a reliable measurement decreases. This possibility was further examined in the combined stimuli examination.

Table 7, below, summarizes the results obtained in the standard protocol development.

TABLE 7

| | | Examination a | | Examination b | | |
|---|---|---|---|---|---|---|
| No | Age & Gen. | PWT at baseline | Type of response | PWT at baseline | Type of response | EDV functioning |
| 1 | 34 F | 42 | Abnormal | 39 | Normal | Normal |
| 2 | 55 F | 21 | Normal | 18 | Normal | Normal |

TABLE 7-continued

| | | Examination a | | Examination b | | |
|---|---|---|---|---|---|---|
| No | Age & Gen. | PWT at baseline | Type of response | PWT at baseline | Type of response | EDV functioning |
| 3 | 23 M | 17 | Normal | 16 | Normal | Normal |
| 4 | 23 M | 26 | Normal | 27 | Normal | Normal |
| 5 | 39 M | 29 | Normal | 21 | Normal | Normal |
| 6 | 57 M | 45 | Abnormal | 37 | Abnormal | Abnormal |
| 7 | 46 F | 24 | Normal | 23 | Abnormal | Normal |
| 8 | 36 F | 33 | Normal | 34 | Normal | Normal |
| 9 | 28 M | 44 | Abnormal | 51 | Abnormal | Abnormal |

It can be seen that only in one out of 9 cases the results differ. In addition, it was found in the 4 cases where the elapsed time was relatively long (>40 ms) during baseline (in examinations a or b), results were abnormal while with shorter elapsed time (<40 ms) it appeared only in 2/14 cases.

Table 8 below shows the effect of a moderate walking on PWT. The obtained results indicate that short and moderate effort of walking shorten elapsed time ($P<0.05$).

TABLE 8

| | PWT | | |
|---|---|---|---|
| No. | before walking [ms] | (1) after walking [ms] | Reduction in PWT [%] |
| 1 | 37.5 | 34.4 | 8.26 |
| 2 | 45.4 | 32.7 | 27.9 |
| 3 | 46.3 | 35.1 | 24.1 |
| 4 | 52.2 | 41.3 | 20.88 |
| 5 | 46.5 | 38.22 | 17.8 |
| Average | 45.8 ± 5.3 | 36.3 ± 3.4 | 19.78 |

(1) $p < 0.05$ between values obtained before and after walking

A Comparison between the ultrasonography examination and the prototype system examination is shown in table 9, below.

TABLE 9

| | Age & gender | Change in vessel diameter | US EDV functioning | Prototype system | | | | |
|---|---|---|---|---|---|---|---|---|
| | | | | Examination a | | Examination b | | |
| | | | | PWT at baseline | Type of response | PWT at baseline | Type of response | [1] EDV functioning |
| 1 | 57 M | 3.6% | Abnormal | 29 | Abnormal | 47 | Abnormal | Abnormal |
| 2 | 56 F | 3.5% | Abnormal | 31 | Abnormal | 33 | Abnormal | Abnormal |
| 3 | 53 F | 27.3% | Normal | 24 | Normal | 23 | Normal | Normal |
| 4 | 42 M | 7.8% | Normal | 42 | Abnormal | 41 | Abnormal | Abnormal |
| 5 | 57 M | 1.8% | Abnormal | 29 | Abnormal | 31 | Abnormal | Abnormal |
| 6 | 57 M | 14.2% | Normal | 33 | Normal | 41 | Abnormal | Normal |
| 7 | 52 M | 19.1% | Normal | 33 | Normal | 28 | Normal | Normal |
| 8 | 39 M | 8.3% | Normal | 29 | Normal | 21 | Normal | Normal |
| 9 | 57 F | 2.7% | Abnormal | 20 | Abnormal | 15 | Abnormal | Abnormal |
| 10 | 41 M | 9.8% | Normal | 25 | Normal | 24 | Abnormal | Normal |
| 11 | 29 M | 4.6% | Abnormal | 46 | Abnormal | 35 | Abnormal | Abnormal |

[1] $p < 0.02$ US vs. the prototype system

AS shown, in 10 out of 11 subjects, the ultrasonography examination and the prototype system examination had similar results ($p<0.02$). In the case of subject 4, where results were contrary, the ultrasonography examination indicated a FMD of 7.8%, which is 1.8% above the borderline of 6%.

Discussion

In the mechanical stimulus examination, two groups were examined. In one group (n=10) subjects had one risk factor at the most for endothelial dysfunction, in the second group (n=11) subjects had at least two risk factors for endothelial dysfunction. The results obtained indicated that in the group with a maximum of one risk factor, 8 out of 10 subjects had normal endothelial function and in the group where subjects had at least two risk factors only 2 out of 11 subjects had normal functioning endothelium ($p<0.002$). The average age in the group that had abnormal endothelium dependent vasoreactivity was found to be significantly higher than the group that was found to have normal endothelium dependent vasoreactivity ($p<0.01$).

In the thermal stimulus examination the elapsed time parameter, PWT, was recorded from the left hand continuously in all individuals examined (n=6). PWT values decreased substantially relatively to baseline ($p<0.001$) and heart rate increased when the right hand was submerged in the cold water (30%-40% decrease in PWT) for a period of 1 minute, When the right hand was submerged for a period of 2 minutes the decrease in PWT relative to the 100% baseline was significantly larger ($p<2.5E-6$) (60%-80% decrease in PWT). There was also a significant difference ($p<0.05$) between the recovery times after the hand was pulled out of the cold water.

The high significant difference (in spite of the small size groups) between control and exposure to cold water is in accordance with the prediction that measurement in the direction of vasoconstriction is a sensitive measurement, in agreement with the Moens-Korteweg equation.

Unexpectedly, results obtained by the prototype system in the lying position and the ultrasonography device were not compatible. Endothelium dependent vasoreactivity function was examined in two different postures (sitting and lying). The results show discrepancies between the data obtained in a sitting posture and that obtained in a lying posture. These findings indicate that there is an additional physical factor that results in a dependence of PWT on posture. In many cases high value of PWT during baseline was followed by relatively low changes of PWT due to reactive hyperemia. This type of result is associated with the mechanical properties of the arterial wall.

To this end a "physiological window" has been defined in which the system has an appropriate mode of operation. It was assumed that in cases where the initial PWT value was relatively high (>40ms), the initial radius before relaxation was also relatively wide. This may explain that the results obtained in a lying position with relatively large initial radius were based on measurements carried out, beyond the "physiological window." Compared to this, cases in which the initial PWT value was relatively low, as in most examinations performed in a sitting position, it is assumed that the examination was performed within the "physiological window". Statistical analysis of the data show that the average PWT during baseline is significantly higher in cases where subjects were found to have abnormal endothelium dependent vasoreactivity compared to cases where subjects were found to have normal endothelium dependent vasoreactivity.

The combined stimuli examination showed that a moderate walk for about 2 minutes before the examination, which causes a moderate elevation and alpha sympathetic activity, led to vasoconstriction and PWT reduction, hence allowed the examination to be conduct within the "physiological window". Intensifying the physical activity (running or jumping) before examination causes an opposite effect in which probably beta receptors are also active causing vasodilatation. In such a case it reduces the probability that the examination will be conducted within the "physiological window."

A comparison between results obtained by the prototype system and ultrasonography was carried out on a study group of 11 subjects. In 10 out of the 11 subjects the diagnoses determined by both the prototype system and the ultrasonography were compatible ($p<0.015$). In one case the US examination indicated a slightly higher value than the borderline increase in brachial diameter (7.8% vs. 6%) while the prototype system indicated "no response" in the first examination and a "weak response" in the second examination. In 5 of the cases both devices indicated abnormal endothelium dependent vasoreactivity and in the 5 other cases both devices indicated normal endothelium dependent vasoreactivity.

Example 3

A Second Prototype System

A second prototype system has been designed and constructed. The system included: (i) a custom designed data logger; (ii) a brachial, radial and carotid transducers, all being operative at low frequencies and based on piezoelectric ceramic elements; (iii) an electrocardiogram chest electrode; (iv) a standard personal computer; and (v) data analysis software (see Example 1).

The custom designed data logger included an amplifier, a four-channel A/D card connected to the computer via a USB cable and a small LCD monitor.

The brachial transducer was a coin shaped transducer, about 2 cm in diameter, attached to a dual compartment sphyngmanometric cuff, so as to allow both arterial occlusion (mechanical stimulus) and attachment of the transducer with a constant and controlled force. The dual compartment sphyngmanometric cuff included two separate air compartments: a low pressure compartment (~20 mmHg) for applying force on the brachial transducer thus coupling the transducer to the skin with a controlled force; and a high pressure compartment (up to 300 mmHg) for applying the mechanical stimulus on the artery. The high-pressure compartment facilitates quick release of pressure.

The radial and carotid transducers were pencil shaped transducers with attached to stabilizing devices facilitating constant applied force for applanation tonometry, where the radial transducer was attached to a wrist stabilizing device and the carotid transducer was attached to a neck stabilizing device.

Example 4

In Vivo Measurements Using the Second Prototype System

In vivo tests were performed on 22 volunteers, using the second prototype system of Example 2.

Mechanical Stimulus

The brachial and the radial transducers were connected to the subject under examination, as further detailed in Example 2. For each subject, two parameters were obtained, the elapsed time parameter, PWT, and the amplitude parameter, PWA (pulse wave amplitude). The examination of each subject also included examination using the ultrasonography device (see further details in Example 2, above).

Figure 12A:
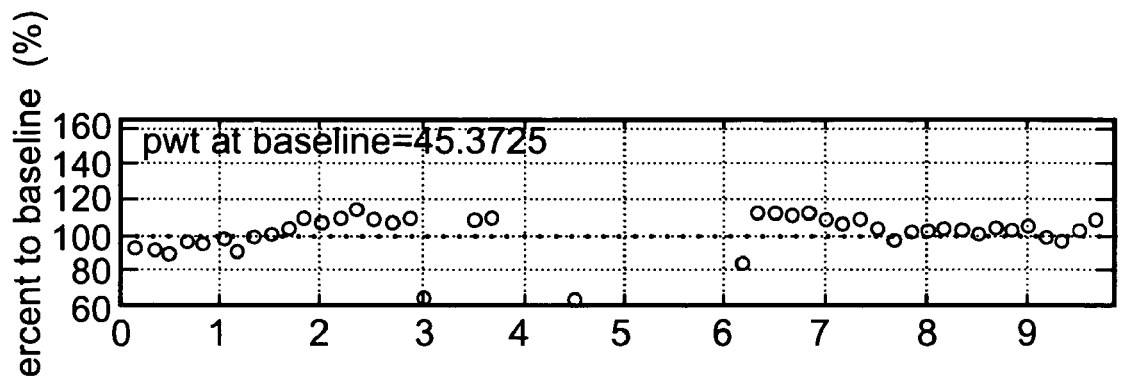
FIGS. 12a-c show the elapsed time (FIG. 12a), standard deviation (FIG. 12b) and amplitude (FIG. 12c) during supine position of a subject, who has been diagnosed by US measurements as having normal endothelial function.
Figure 12B:
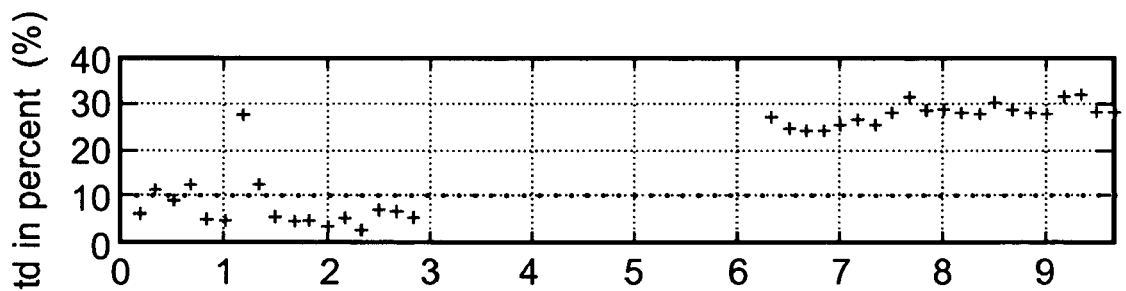
Figure 12C:
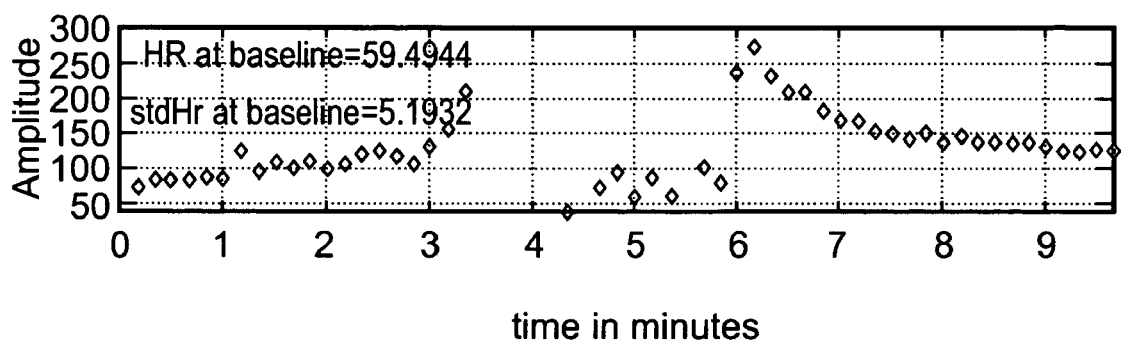

FIGS. 12a-c show the elapsed time (FIG. 12a), standard deviation (FIG. 12b) and amplitude (FIG. 12c) during supine position of a subject who has been diagnosed by US measurements as having normal endothelial function. The brachial artery was occluded for three minutes. After reopening of the occlusion (6 min) elapsed time showed only minor change while the amplitude showed dramatic changes. The value of PWT was relatively long, about 45 ms.

FIGS. 13a-c show the elapsed time (FIG. 13a), standard deviation (FIG. 13b) and amplitude (FIG. 13c) during sitting position of a subject who has been diagnosed by US measurements as having normal endothelial function. The brachial artery was occluded for three minutes. As shown, in this case the elapsed time was increased and almost no change in the amplitude. The value of PWT was relatively small, about 15 ms, indicating that the initial diameter of the artery was relatively small.

Figure 14A:
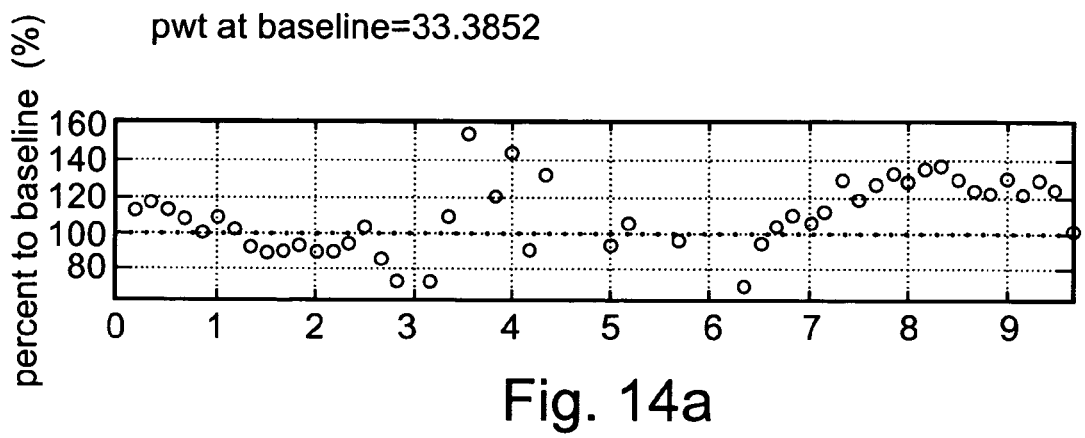
FIGS. 14a-c show the elapsed time (FIG. 15a), standard deviation (FIG. 15b) and amplitude (FIG. 15c) during sitting position of another subject who has been diagnosed by US measurements as having normal endothelial function.
Figure 14B:
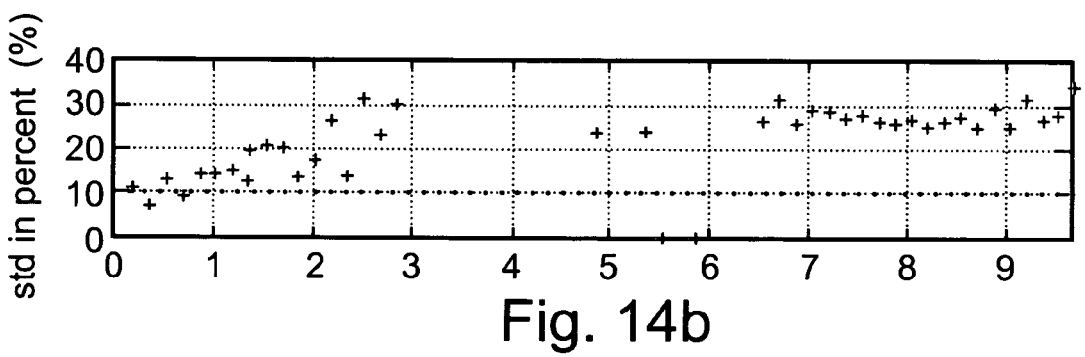
Figure 14C:
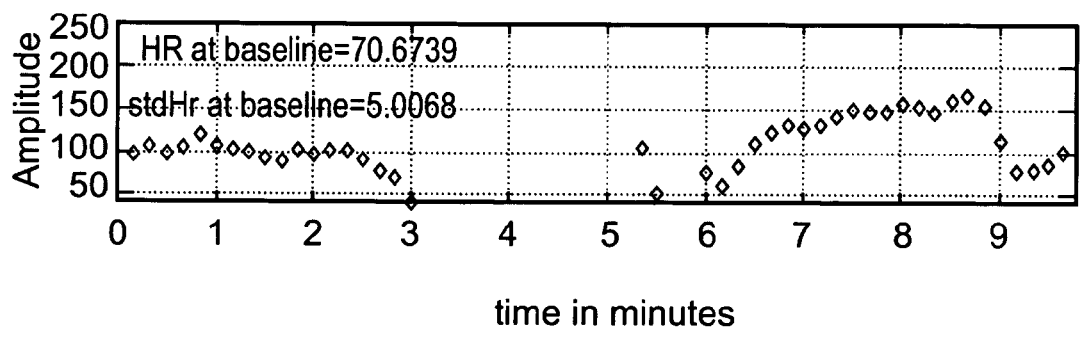

FIGS. 14a-c show the elapsed time (FIG. 15a), standard deviation (FIG. 15b) and amplitude (FIG. 15c) during sitting position of another subject who has been diagnosed by US measurements as having normal endothelial function. The value of PWT was small, about 33 ms, indicating that the measurement was initiated within the "physiological window." With the increment of the artery's radius, a non-linear region, characterized by a non-linear amplitude increment, was observed.

Figure 15A:
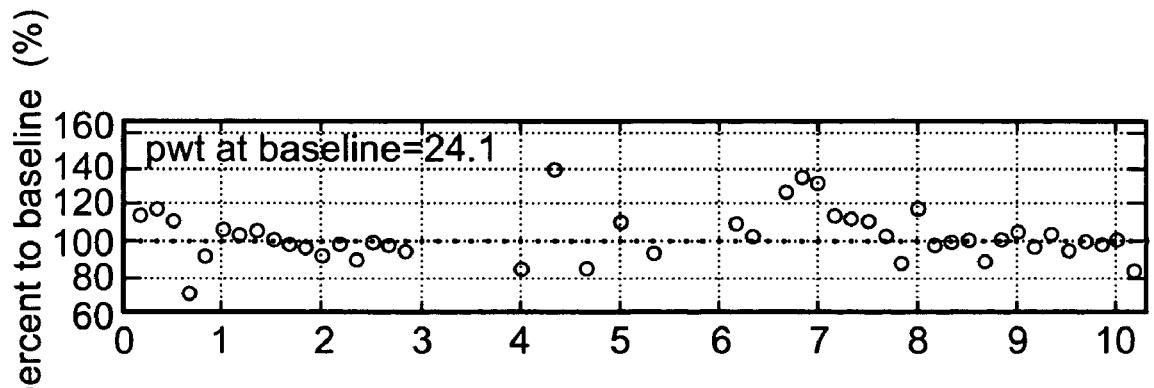
FIGS. 15a-c show the elapsed time (FIG. 14a), standard deviation (FIG. 14b) and amplitude (FIG. 14c) during sitting position of a subject who has been diagnosed by US measurements as having abnormal endothelial function.
Figure 15B:
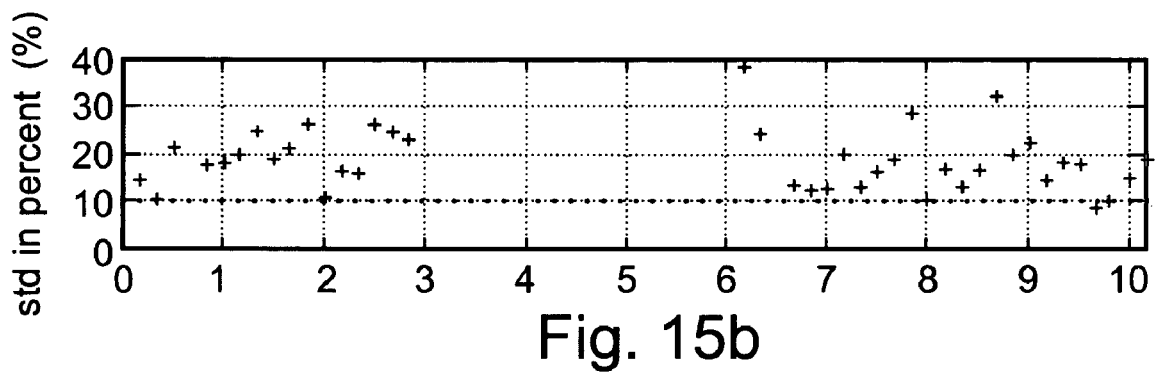
Figure 15C:
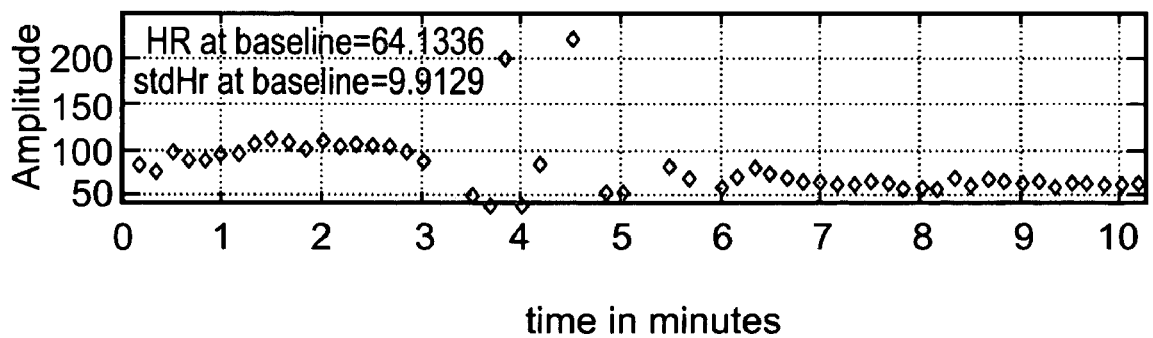

FIGS. 15a-c show the elapsed time (FIG. 14a), standard deviation (FIG. 14b) and amplitude (FIG. 14c) during sitting position of a subject who has been diagnosed by US measurements as having abnormal endothelial function. As shown, in this case no change was observed in the elapsed time or in the amplitude, indicating abnormal endothelial function. The value of PWT was short, about 24 ms, indicating that the measurement was carried out within the above mentioned "physiological window."

Chemical Stimulus

The effect of a chemical stimulus was tested on three subjects pretreated by with nitroglycerin.

Figure 16A:
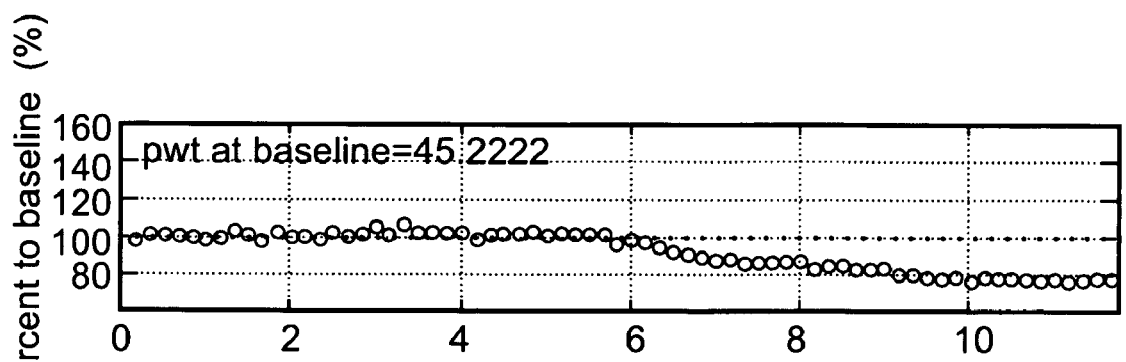
FIGS. 16a-c show the elapsed time (FIG. 16a), standard deviation (FIG. 16b) and amplitude (FIG. 16c) after a chemical stimulus using nitroglycerin and during supine position of a subject who has been diagnosed by US measurements as having normal endothelial function.
Figure 16B:
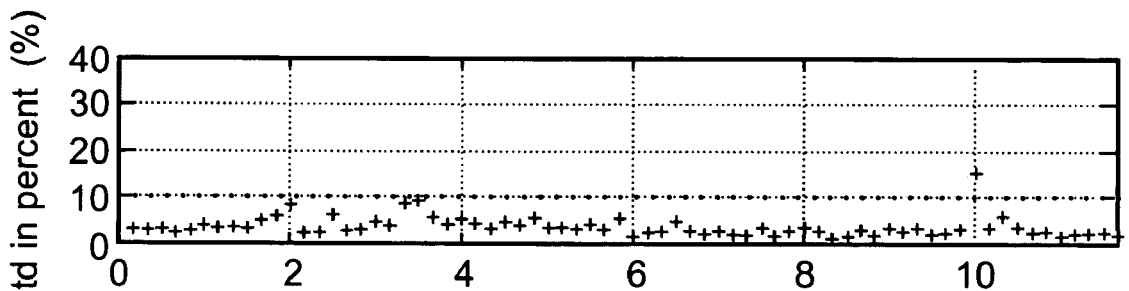
Figure 16C:
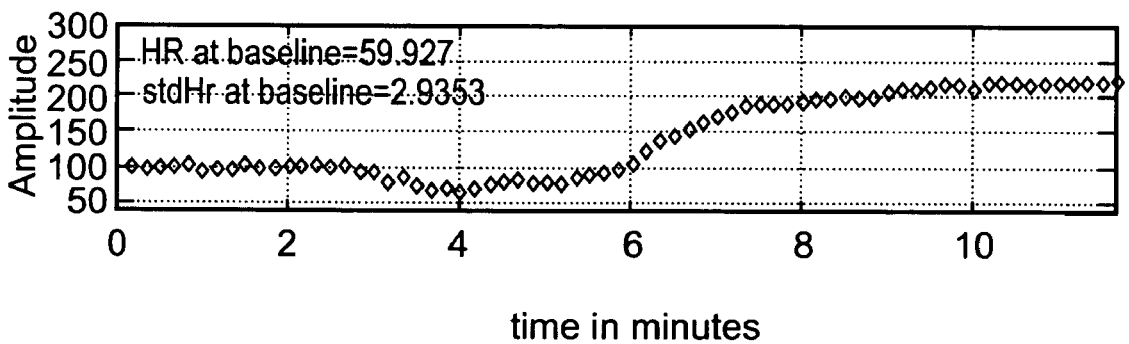

FIGS. 16a-c show the elapsed time (FIG. 16a), standard deviation (FIG. 16b) and amplitude (FIG. 16c) after the nitroglycerin treatment and during supine position of a subject who has been diagnosed by US measurements as having normal endothelial function. As shown, in this case the elapsed time was reduced and the amplitude was increased. The value of PWT was relatively large, about 45 ms, indicating that the initial diameter of the artery was relatively wide.

Table 10, below, summarize the results for all subjects under examination:

TABLE 10

| | Second Prototype System | | | |
|---|---|---|---|---|
| | US | PWT | PWA | PWT and PWA |
| Normal Response | 14 | 9 | 5 | 14 |
| Abnormal Response (*) | 5 | 6 | 6 | 6 |
| Border zone results | 3 | 0 | 2 | 2 |
| Total | 22 | 15 | 13 | 22 |

(*) In both PWT and PWA parameters.
Spearman correlation, r = 0.93, p < 0.001.

Discussion

In this example, in addition to the elapsed time parameter, the amplitude parameter was included in analysis procedure. As stated in the discussion of Example 2, the measurement of endothelial function was based on the change of elapsed time parameter thereby requiring the measurement to be carried out within the "physiological window," where the initial radius of the artery diameter is sufficiently small. Under such conditions, the elasticity module of the artery's wall is, to a good approximation, constant causing a linear dependence of the pulse wave velocity on the inverse of the radius (the pulse wave velocity decreased as the arterial radius is increased).

With the addition of pulse wave amplitude to the analysis, sensitivity to changes in artery diameter even beyond the "physiological window"was found. The amplitude parameter was increased for relatively large radius, indicating the participation of collagen in the change. At the same time, no change was observed in elapsed time parameter. On the other hand, no change in the amplitude parameter was observed when the initial radius size was considered to be within the "physiological window."

Example 5

Measuring Heart Rate Variability Using Electrocardiogram Leads

Heart rate variability analysis was carried out in 12 of the subjects who had undergone examination for the endothelial dysfunction measurement of Example 4. In 10 subjects heart rate variability analysis indicated normal autonomic nervous system activity and therefore possible normal coronary function. The analysis is based on 3 min recording using electrocardiogram lead II of the chest of the subjects, during baseline (before application of the mechanical stimulus).

The results are presented in FIGS. 17a-h.

FIGS. 17a, 17c, 17e, and 17g show heart rate variability analysis of a subject with normal heart rate variability activity and endothelial dysfunction. FIGS. 17b, 17d, 17f, and 17h show heart rate variability analysis of a subject with abnormal activity but with normal brachial endothelial function. Endothelial function or dysfunction are not shown in FIGS. 17a-h.

Figure 17A:
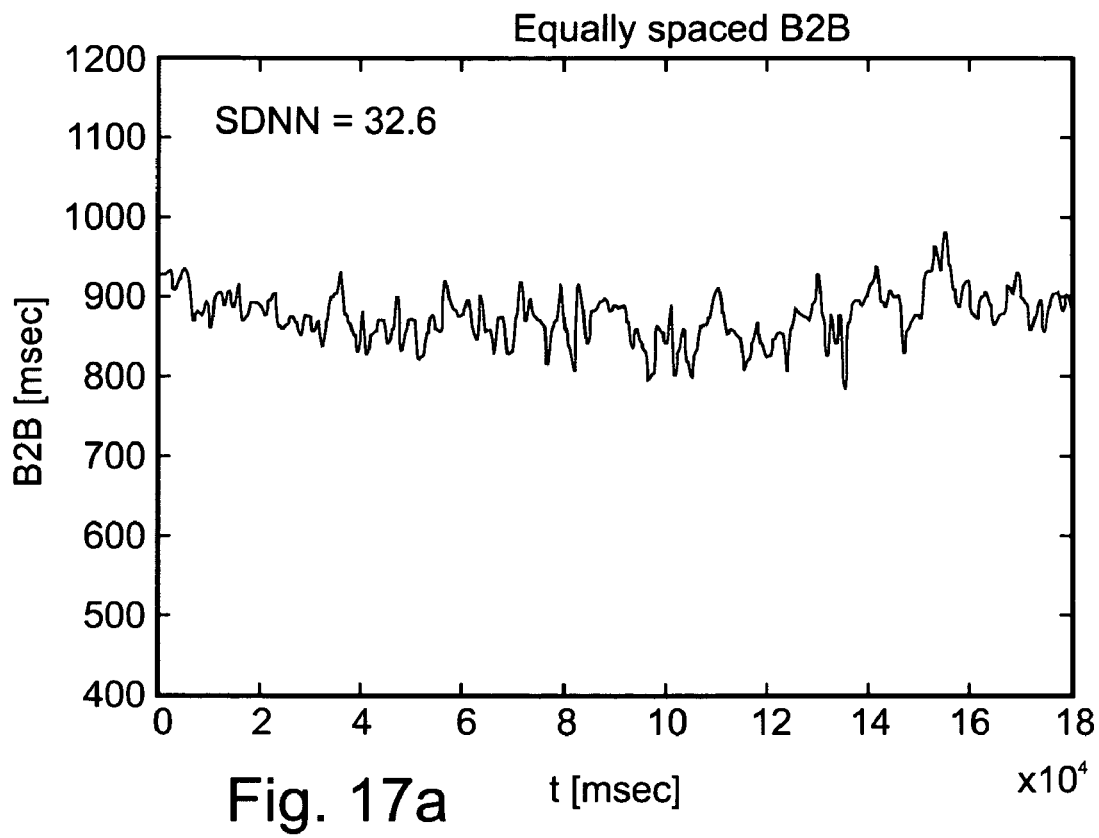
FIGS. 17a-h show results of heart rate variability analysis of a subject having normal autonomic nervous system activity and endothelial dysfunction (17a, 17c, 17e and 17g) and a subject having abnormal autonomic nervous system activity and normal brachial endothelial function (17b, 17d, 17f and 17h)
Figure 17B:
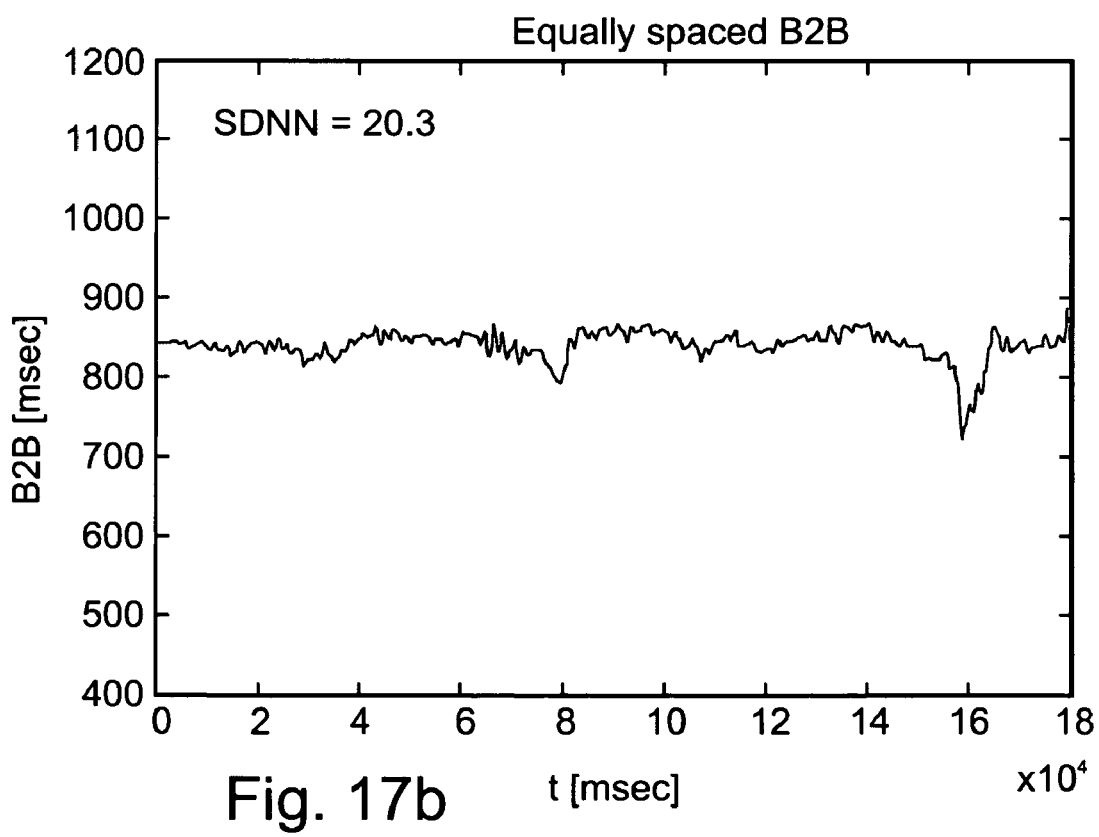

FIGS. 17a-b show beat-to-beat analysis, referred to hereinafter as B2B analysis. For the subjects with the differences between subjects with normal and abnormal heart rate variability activity are manifested by the value of SDNN, which is in the normal range in FIG. 17a and significantly lower in FIG. 17b. As stated, a reduced value of SDNN reflects a reduced parasympathetic activity. In addition, high fluctuations between beats are shown in FIG. 17a, compared to FIG. 17b.

Figure 17C:
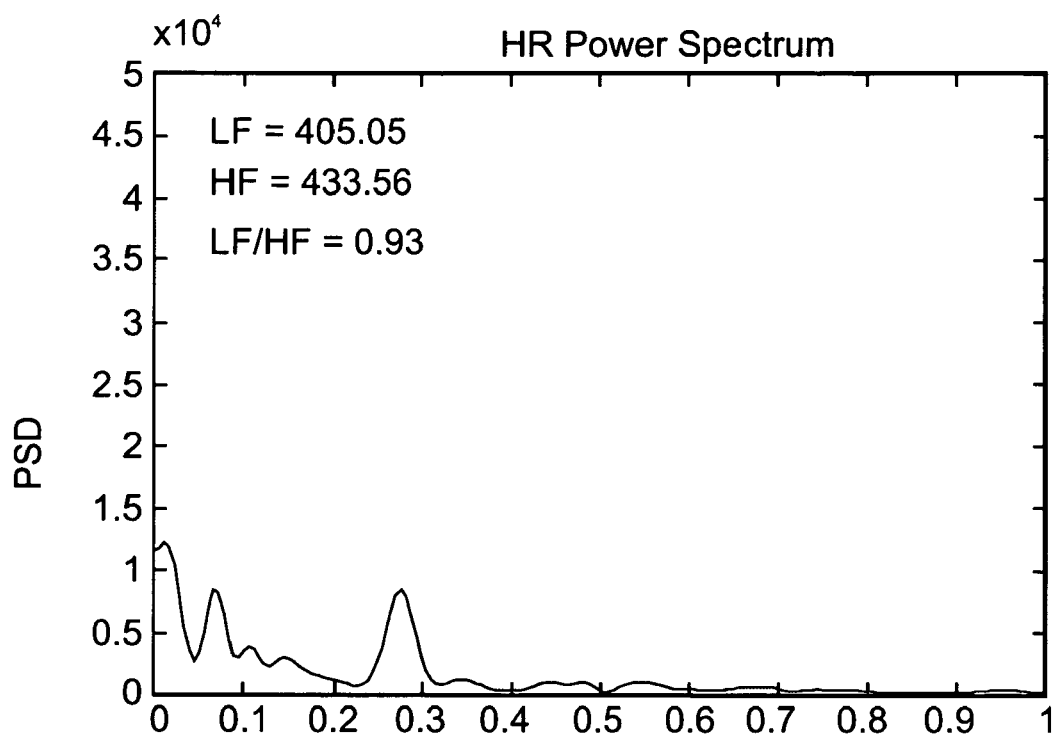
Figure 17D:
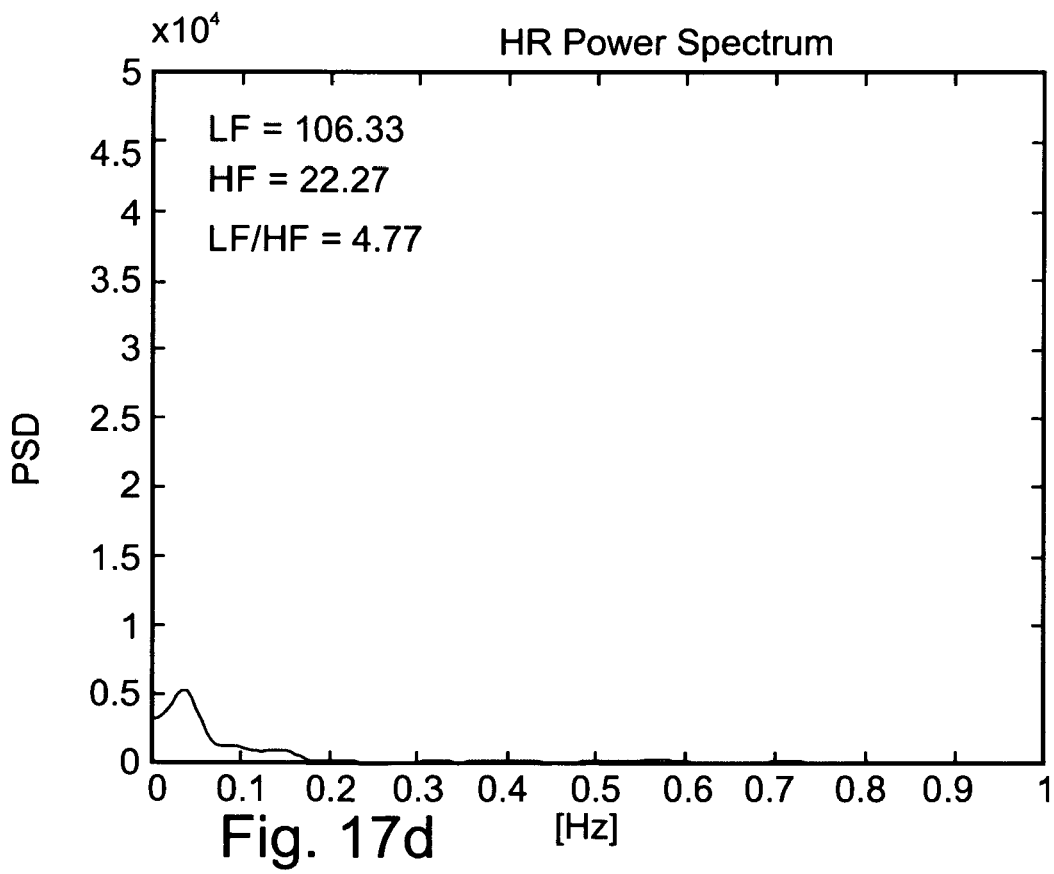

FIGS. 17c-d show the power spectrum densities. The normal HF peak around 0.3 Hz shown for the normal subject (FIG. 17c) is absent from FIG. 17d, hence indicates abnormal heart rate variability. In addition, HF value is relatively high in FIG. 17c compared to FIG. 17d, LF/HF is low in FIG. 17c compared to FIG. 17d, hence also supporting the abnormal heart rate variability diagnosis of the subject of FIG. 17d.

Figure 17E:
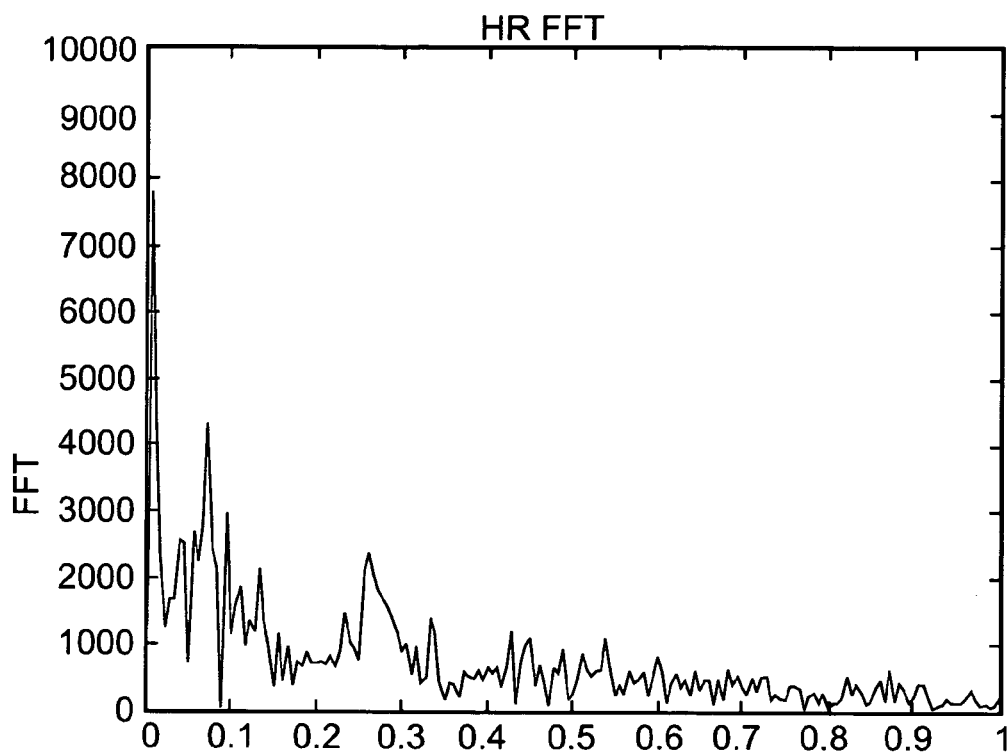
Figure 17F:
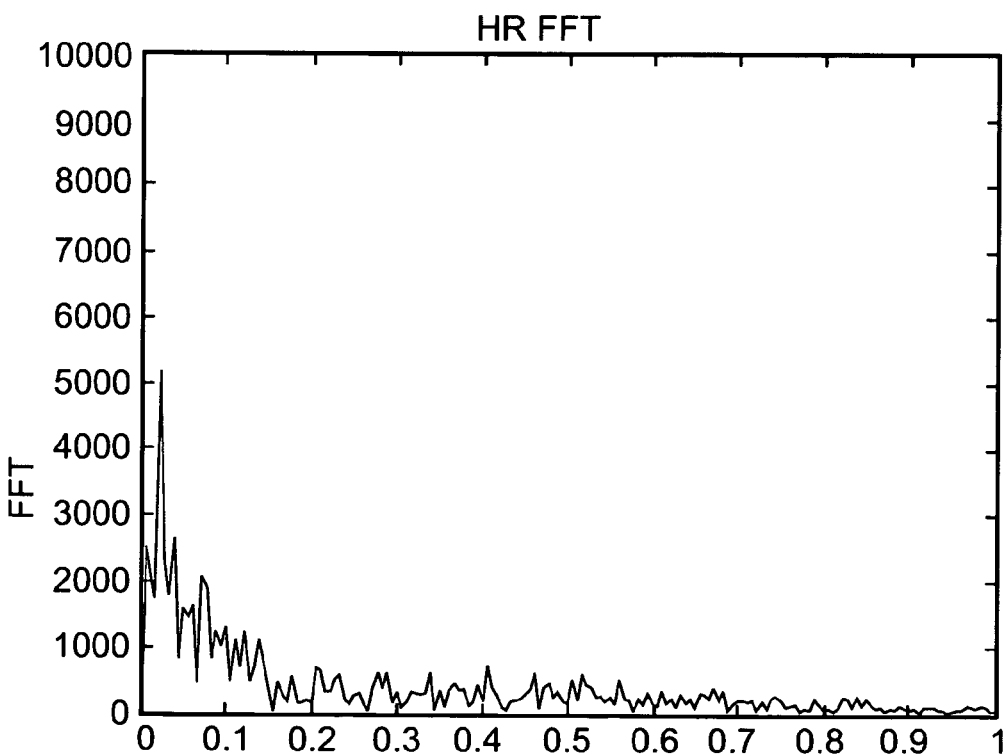

FIGS. 17e-f show Fast Fourier Transform analysis of the RRI series. Again, a clear peak shown around 0.3 Hz in FIG. 17e, is almost completely absent in FIG. 17f.

Figure 17G:
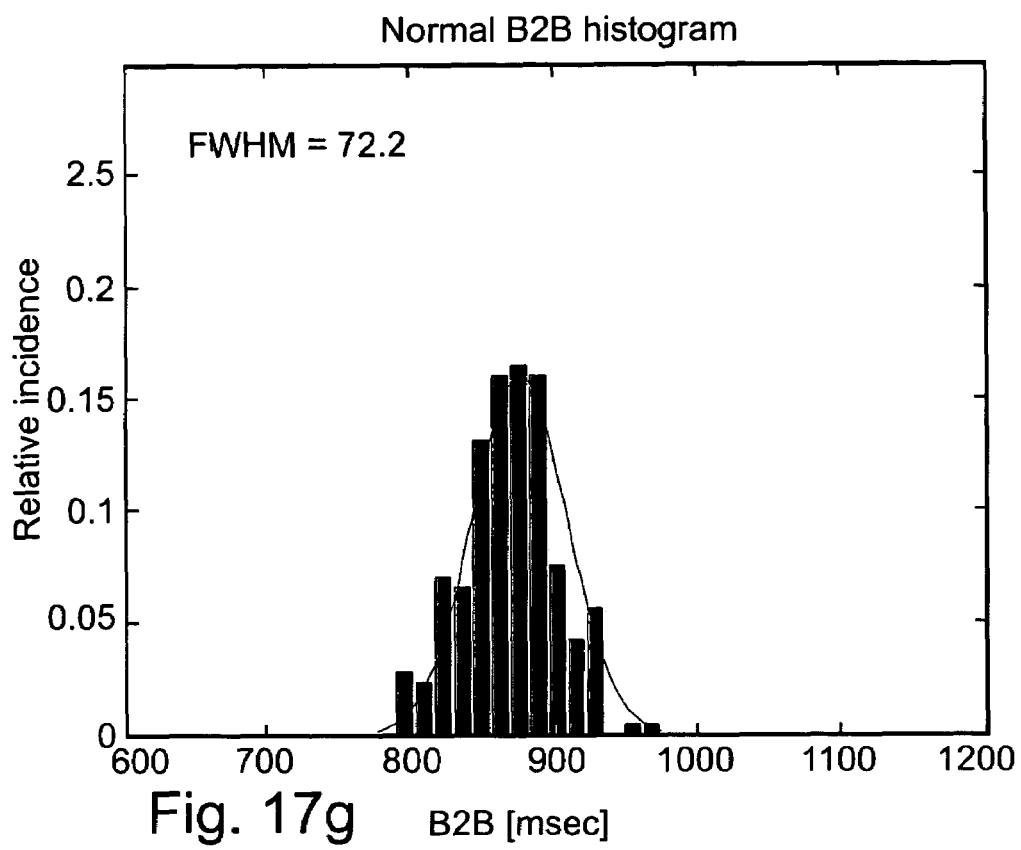
Figure 17H:
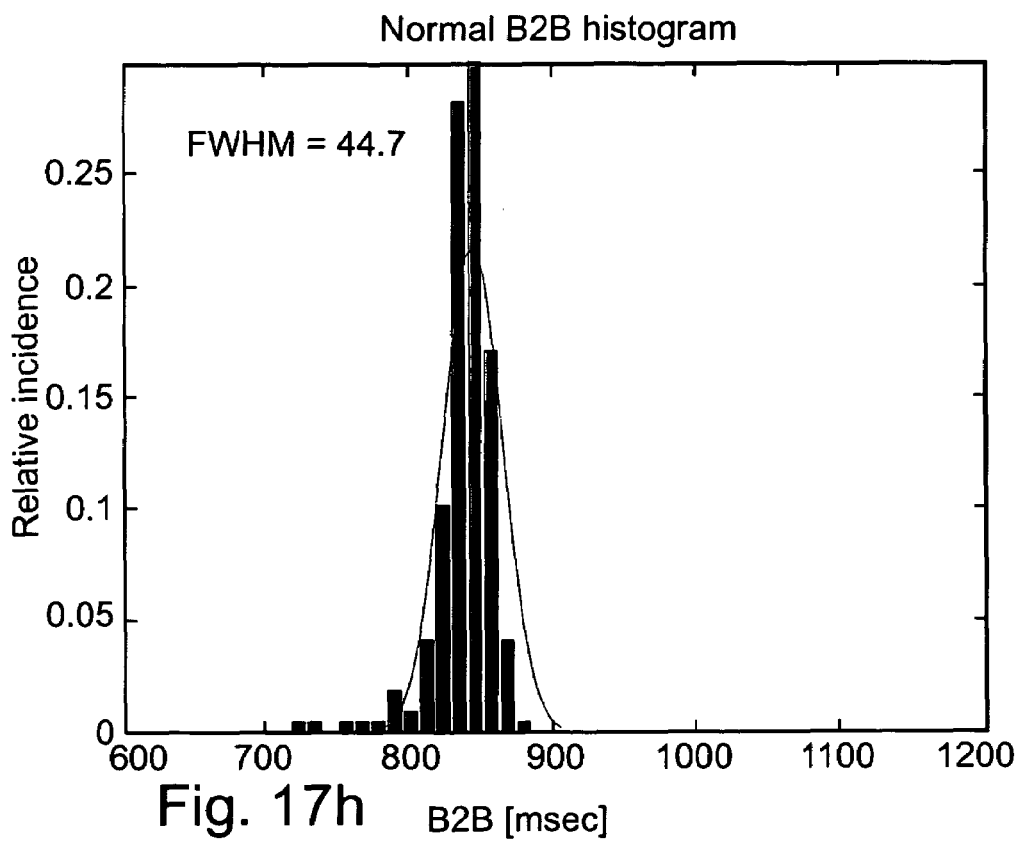

FIGS. 17g-h show relative incidence, as a function of B2B (measured in ms). A relatively wide histogram of time intervals between beats is presented in FIG. 17g, compared to the narrow histogram shown in FIG. 17h, indicating normal heart rate variability for the subject of FIG. 17g and abnormal heart rate variability for the subject of FIG. 17h.

Example 6

Cold Pressure Test

In this study, a cold pressure test was performed on nine young subjects, 24-35 years of age (30.8±3.8 years) having no known risk factors for coronary heart disease hence assumed to have normal endothelial function.

Four channels were connected: electrocardiogram lead II, connected to the chest, and three transducers, connected to the brachial, radial and carotid arteries. Sample rate for all the channels was 1000 Hz. The examination was performed in a temperature-controlled room (22° C.). Blood pressure was measured with an automated sphyngo-manometer before the recording.

The recording protocol included the following periods of thermal stimuli: 3 minutes at room temperature, 4 minutes at 25° C., 2 minutes at 5° C. and 10 minutes at 25° C. Each stimulus was applied by a bath containing water in the respective temperature, in which the subjects placed the right wrist.

For each subject, the following parameters were extracted: $T_1$ (brachial-radial transit time), $T_2$ (QRS-carotid transit time), three amplitude parameters (one for each artery and heart rate.

Figure 18A:
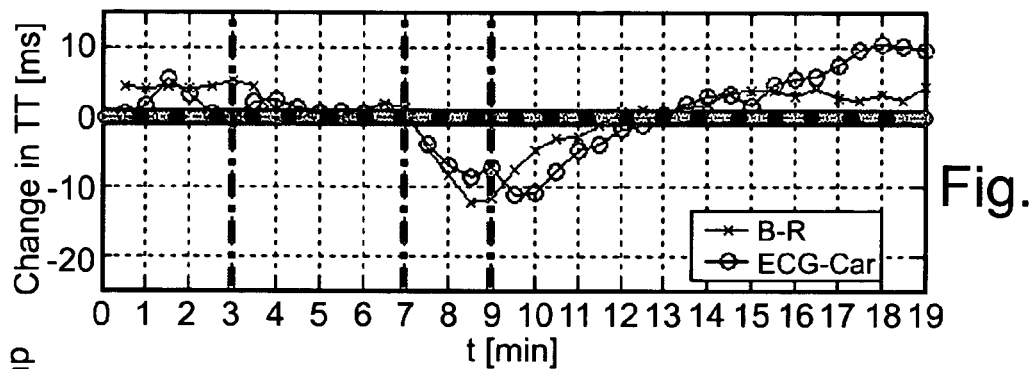
FIGS. 18a-c show changes of two elapsed time parameters (FIG. 18a), three amplitude parameters (FIG. 18b) and heart rate (FIG. 18c), during a cold pressure test.
Figure 18B:
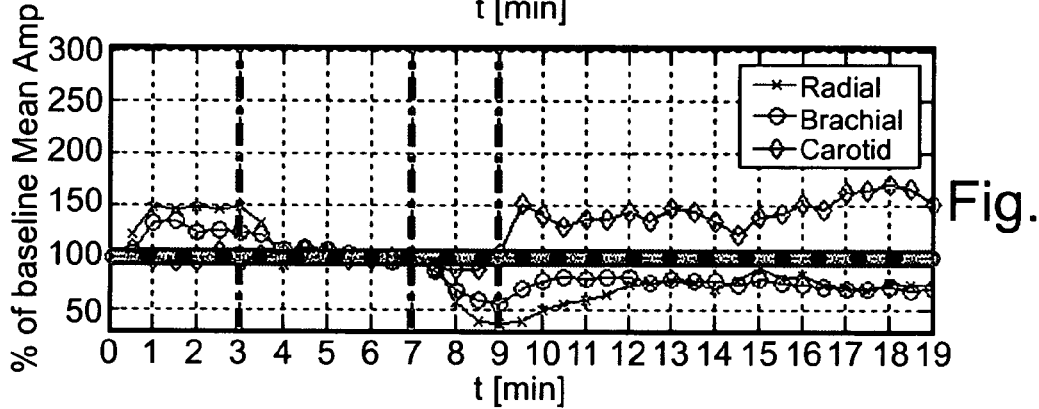
Figure 18C:
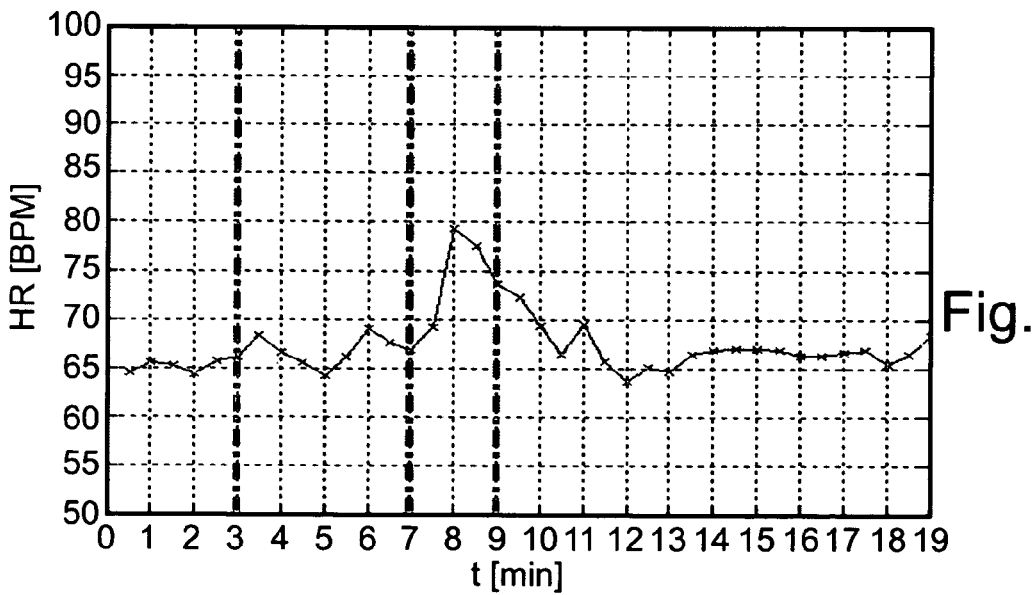

FIGS. 18a-c show the results of the examination, where transitions between the steps of the protocols are designated by dashed vertical lines at t=3, 7 and 9 minutes.

FIG. 18a shows changes of the two elapsed time parameters $T_1$ (blue line) and $T_2$ (red line), measured in ms. As shown, both $T_1$ and $T_2$ restore and continue to increase above their original (baseline) values during recovery, indicating normal endothelial function, as further detailed hereinabove.

FIG. 18b shows changes of all three amplitudes, measured as percentage of the baseline value. A decrement in all amplitudes is observed during the low temperature period (7<t<9 min). As shown the decrement in the amplitude of the pulse measured of the carotid artery is less pronounced than the decrement in the amplitudes measured of the brachial and radial arteries. During recovery, all amplitudes exhibit an increment, where the increment in the amplitude of the pulse measured of the carotid artery is more pronounced, and reaches a value of about 50% above baseline. The increments in the amplitudes of the pulse measured of the brachial and radial arteries are less pronounced and reach about 10-20% below baseline.

FIG. 18c shows the heart rate, measured in bits/min. A clear peak was observed during the low temperature period (7<t<9 min), indicating increased sympathetic activity. A minor heart rate increment was also observed during the first transition (from room temperature to 25° C.). As shown in FIG. 18c the heart rate resorted its baseline value during the second recovery period (9<t<19 min).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of determining endothelial dependent vaso-activity of a subject, the method comprising:
   recording pressure-related signals of a plurality of locations adjacent to at least one blood vessel;
   extracting parameters from said pressure-related signals, said parameters comprise a first parameter, sensitive to arterial radius changes at the initial stage of arterial dilatation, and a second parameter, sensitive to arterial radius changes at larger arterial dilatation;

using said parameters to determine a change of at least one characteristic of said at least one blood vessel, said change being representative of endothelial functioning;

determining the endothelial dependent vasoactivity of the subject using said parameters; and displaying at least an indication of said endothelial dependent vasoactivity.

2. The method of claim 1, further comprising determining an autonomic nervous system activity of the subject.

3. The method of claim 2, further comprising correlating said endothelial functioning and said autonomic nervous system activity, so as to obtain a correlation function, and using said correlation function to at least preliminarily determine the endothelial dependent vasoactivity of the subject.

4. The method of claim 2, wherein said determining of said autonomic nervous system activity comprises heart rate variability analysis of said pressure-related signals.

5. The method of claim 2, wherein said determining of said autonomic nervous system activity comprises recording electrocardiogram signals of a chest of the subject and performing heart rate variability analysis of said electrocardiogram signals, thereby determining said autonomic nervous system activity.

6. The method of claim 5, further comprising determining a pre-ejection period and valve-artery period.

7. The method of claim 6, wherein said valve of said valve-artery period is an aortic valve and said artery of said valve-artery period is a carotid artery.

8. The method of claim 6, wherein said determination of said pre-ejection period and said valve-artery period, comprises determining an elapsed time between peaks of said electrocardiogram signals and peaks of said pressure-related signals.

9. The method of claim 8, wherein said peaks of said electrocardiogram signals comprise QRS peaks.

10. The method of claim 5, wherein said at least one parameter is selected from the group consisting of an amplitude of said pressure-related signals, a width of said pressure-related signals, an elapsed time between two peaks of said pressure-related signals and an elapsed time between peaks of said electrocardiogram signals and peaks of said pressure-related signals.

11. The method of claim 1, further comprising stimulating said at least one blood vessel.

12. The method of claim 11, wherein said stimulating of said at least one blood vessel is effected by a procedure selected from the group consisting of a mechanical stimulation, a thermal stimulation a chemical stimulation, an electrical stimulation a mental stress stimulation and a physical exercise stimulation.

13. The method of claim 11, wherein said stimulating of said at least one blood vessel comprises applying external pressure on said at least one blood vessel.

14. The method of claim 11, wherein said stimulating of said at least one blood vessel comprises reducing a temperature of said at least one blood vessel.

15. The method of claim 1, wherein said at least one blood vessel is selected from the group consisting of a brachial artery, a radial artery and a carotid artery.

16. The method of claim 1, wherein said recording of said pressure-related signals comprises piezoelectric ceramic elements.

17. The method of claim 1, wherein said recording of said pressure-related signals comprises a membrane-based sensor.

18. The method of claim 17, wherein said membrane-based sensor is an electrate microphone.

19. The method of claim 1, further comprising obtaining a frequency decomposition of said at least one parameter, and using said frequency decomposition for determining the endothelial dependent vasoactivity of the subject.

20. The method of claim 1, wherein said at least one parameter is selected from the group consisting of an amplitude of said pressure-related signals, a width of said pressure-related signals and an elapsed time between two peaks of said pressure-related signals.

21. The method of claim 20, further comprising obtaining a frequency decomposition of said amplitude, and using said frequency decomposition for determining the endothelial dependent vasoactivity of the subject.

22. The method of claim 20, further comprising obtaining a frequency decomposition of said width, and using said frequency decomposition for determining the endothelial dependent vasoactivity of the subject.

23. The method of claim 20, further comprising obtaining a frequency decomposition of said elapsed time, and using said frequency decomposition for determining the endothelial dependent vasoactivity of the subject.

24. The method of claim 1, wherein said at least one characteristic of said at least one blood vessel is selected from the group consisting of a radius of said at least one blood vessel and an elastic modulus of said at least one blood vessel.

25. The method of claim 1, wherein said extracting of said at least one parameter comprises:

(a) scanning pressure-related signals recorded of a first location and detecting a first peak;

(b) scanning pressure-related signals recorded of a second location and detecting a second peak corresponding to said first peak;

(c) measuring an elapsed time between said first peak and said second peak; and (d) repeating said steps (a)-(c) at least once.

26. The method of claim 1, wherein said first parameter is an amplitude of a pressure related signal.

27. The method of claim 1, wherein said second parameter is an elapsed time between peaks of a pressure related signal and an ECG signal.

28. A system for determining endothelial dependent vasoactivity of a subject, the system comprising:

an arrangement of sensors for recording pressure-related signals of a plurality of locations adjacent to at least one blood vessel;

a processing unit operable to receive, record and process said pressure-related signals and configured to display results of said processing;

said processing unit being designed and programmed to extract parameters from said pressure-related signals, and to use said parameters to determine a change of at least one characteristic of said at least one blood vessel, said change being representative of endothelial functioning, wherein the parameters extracted from the pressure-related signals comprise a first parameter, sensitive to arterial radius changes at the initial stage of arterial dilatation, and a second parameter, sensitive to arterial radius changes at larger arterial dilatation.

29. The system of claim 28, further comprising electronic-calculation functionality for determining an autonomic nervous system activity of the subject.

30. The system of claim 29, wherein said processing unit is operable to calculate heart rate variability from said pressure-related signals thereby to determine said autonomic nervous system activity.

31. The system of claim 29, further comprising at least one electrocardiogram lead.

32. The system of claim 31, wherein said processing unit is operable to calculate heart rate variability from electrocardiogram signals sensed by said at least one electrocardiogram lead, thereby to determine said autonomic nervous system activity.

33. The system of claim 31, wherein said at least one parameter is selected from the group consisting of an amplitude of said pressure-related signals, a width of said pressure-related signals, an elapsed time between two peaks of said pressure-related signals and an elapsed time between peaks of electrocardiogram signals and peaks of said pressure-related signals.

34. The system of claim 31, wherein said cardioelectrogram lead is designed to be connectable to a chest of the subject.

35. The system of claim 28, further comprising a mechanism for stimulating said at least one blood vessel.

36. The system of claim 35, wherein said mechanism for stimulating said at least one blood vessel is selected from the group consisting of a mechanical mechanism, a thermal mechanism, a chemical mechanism an electrical mechanism, a mechanism for generating mental stress and a device for allowing the subject to perform physical exercise.

37. The system of claim 35, wherein said mechanism is operable to apply external pressure on said at least one blood vessel.

38. The system of claim 37, wherein said mechanism comprises a sphingomanometer.

39. The system of claim 35, wherein said mechanism is operable to reduce a temperature of said at least one blood vessel.

40. The system of claim 39, wherein said mechanism is selected from the group consisting of a bath of fluid and a cuff of fluid, said fluid being at a predetermined temperature.

41. The system of claim 28, wherein said at least one blood vessel is selected from the group consisting of a brachial artery, a radial artery and a carotid artery.

42. The system of claim 28, wherein said sensors comprise at least one piezoelectric ceramic element.

43. The system of claim 28, wherein said sensors comprise at least one membrane-based sensor.

44. The system of claim 43, wherein said sensors comprise at least one electrate microphone.

45. The system of claim 28, further comprising a spectral analyzer for analyzing said at least one parameter and obtaining a frequency decomposition of said at least one parameter, said frequency decomposition being representative of the endothelial dependent vasoactivity of the subject.

46. The system of claim 28, wherein said at least one parameter is selected from the group consisting of an amplitude of said pressure-related signals, a width of said pressure-related signals and an elapsed time between two peaks of said pressure-related signals.

47. The system of claim 28, wherein said at least one characteristic of said at least one blood vessel is selected from the group consisting of a radius of said at least one blood vessel and an elastic modulus of said at least one blood vessel.

48. The system of claim 28, wherein said first parameter is an amplitude of a pressure related signal.

49. The system of claim 28, wherein said second parameter is an elapsed time between peaks of a pressure related signal and an ECG signal.

50. A method of determining endothelial dependent vasoactivity of a subject, the method comprising:
（a) applying a first stimulus to at least one blood vessel;
(b) measuring a pulse wave velocity of blood flowing in said at least one blood vessel;
(c) determining an autonomic nervous system activity of the subject;
(d) correlating said pulse wave velocity and said autonomic nervous system activity, so as to obtain a correlation function having an index;
(e) if said index has a predetermined value then:
(i) applying a second stimulus on said at least one blood vessel; and
(ii) repeating said steps (b)-(c); and thereby determining the endothelial dependent vasoactivity of the subject; and
(f) displaying at least an indication of the endothelial dependent vasoactivity of the subject, wherein said step (e) further comprises applying said second stimulus on at least one additional blood vessel and repeating said steps (b)-(c) for said at least one additional blood vessel.

51. The method of claim 50, wherein said stimulus comprises external pressure.

52. The method of claim 50, wherein said stimulus comprises temperature reduction.

53. The method of claim 50, wherein said at least one blood vessel is selected from the group consisting of a brachial artery, a radial artery and a carotid artery.

54. The method of claim 50, wherein said at least one additional blood vessel is selected from the group consisting of a brachial artery, a radial artery and a carotid artery.

55. The method of claim 50, wherein said determining of said autonomic nervous system activity comprises heart rate variability analysis of said pressure-related signals.

56. The method of claim 50, wherein said determining of said autonomic nervous system activity comprises recording electrocardiogram signals of a chest of the subject and performing heart rate variability analysis of said electrocardiogram signals, thereby determining said autonomic nervous system activity.

57. The method of claim 50, wherein said measuring a pulse wave velocity comprises recording pressure-related signals using piezoelectric ceramic elements.

58. The method of claim 50, wherein said wherein said measuring a pulse wave velocity comprises recording pressure-related signals using a membrane-based sensor.

59. A method of determining endothelial dependent vasoactivity of a subject, the method comprising:
(a) applying a first stimulus to at least one blood vessel;
(b) measuring a pulse wave velocity of blood flowing in said at least one blood vessel;
(c) determining an autonomic nervous system activity of the subject;
(d) correlating said pulse wave velocity and said autonomic nervous system activity, so as to obtain a correlation function having an index;
(e) if said index has a predetermined value then:
(i) applying a second stimulus on said at least one blood vessel; and
(ii) repeating said steps (b)-(c); and thereby determining the endothelial dependent vasoactivity of the subject; and (f) displaying at least an indication of the endothelial dependent vasoactivity of the subject, wherein said first and said second stimuli are each independently selected from the group consisting of a stimulus, a thermal stimulus, a chemical stimulus, an electrical stimulus, a mental stress stimulus and a physical exercise stimulus.

* * * * *